US012285504B2

(12) United States Patent
Moose et al.

(10) Patent No.: US 12,285,504 B2
(45) Date of Patent: Apr. 29, 2025

(54) DISPERSIBLE NONWOVEN MATERIALS INCLUDING CMC-BASED BINDERS

(71) Applicant: GLATFELTER CORPORATION, Charlotte, NC (US)

(72) Inventors: Ronald T. Moose, Lakeland, TN (US); Jacek K. Dutkiewicz, Cordova, TN (US); Alan J. Campbell, Germantown, TN (US)

(73) Assignee: Glatfelter Corporation, Charlotte, NC (US)

( * ) Notice: Subject to any disclaimer, the term of this patent is extended or adjusted under 35 U.S.C. 154(b) by 554 days.

(21) Appl. No.: 17/633,897

(22) PCT Filed: Aug. 5, 2020

(86) PCT No.: PCT/IB2020/057398
§ 371 (c)(1),
(2) Date: Feb. 8, 2022

(87) PCT Pub. No.: WO2021/024199
PCT Pub. Date: Feb. 11, 2021

(65) Prior Publication Data
US 2022/0287925 A1  Sep. 15, 2022

Related U.S. Application Data

(60) Provisional application No. 62/884,236, filed on Aug. 8, 2019.

(51) Int. Cl.
| | | |
|---|---|---|
| A61K 8/02 | (2006.01) | |
| A61K 8/20 | (2006.01) | |
| A61K 8/73 | (2006.01) | |
| A61K 8/86 | (2006.01) | |
| A61Q 19/10 | (2006.01) | |
| D04H 1/425 | (2012.01) | |

(Continued)

(52) U.S. Cl.
CPC .............. *A61K 8/0208* (2013.01); *A61K 8/20* (2013.01); *A61K 8/731* (2013.01); *A61K 8/86* (2013.01); *A61Q 19/10* (2013.01); *D04H 1/425* (2013.01); *D04H 1/587* (2013.01); *D04H 1/64* (2013.01)

(58) Field of Classification Search
None
See application file for complete search history.

(56) References Cited

U.S. PATENT DOCUMENTS

| | | |
|---|---|---|
| 5,281,306 A | 1/1994 | Kakiuchi |
| 5,543,215 A | 8/1996 | Hansen |
| 2003/0096910 A1 | 5/2003 | Soerens et al. |

(Continued)

FOREIGN PATENT DOCUMENTS

| | | |
|---|---|---|
| CN | 1399524 | 2/2003 |
| CN | 1930345 | 3/2007 |

(Continued)

*Primary Examiner* — Arti Singh-Pandey
(74) *Attorney, Agent, or Firm* — Blank Rome LLP

(57) ABSTRACT

Nonwoven materials having at least one layer comprising cellulose fibers, synthetic fibers, or combinations thereof are provided. Such nonwoven materials are at least partially covered on their surface with a binder including carboxymethyl cellulose (CMC) and a metallic salt, the binder having a pH of from about 4.3 to about 4.5. Nonwoven materials including such binder provide for increased wet strength and dispersibility and are suitable for use in a variety of applications, including wipes.

18 Claims, 6 Drawing Sheets

(51) Int. Cl.
*D04H 1/587* (2012.01)
*D04H 1/64* (2012.01)

(56) References Cited

U.S. PATENT DOCUMENTS

| | | |
|---|---|---|
| 2003/0207639 A1 | 11/2003 | Lin |
| 2016/0051115 A1 | 2/2016 | Smith |
| 2021/0054548 A1 | 2/2021 | Salam et al. |

FOREIGN PATENT DOCUMENTS

| | | |
|---|---|---|
| CN | 102971126 | 3/2013 |
| CN | 103298990 | 9/2013 |
| JP | H02149237 | 6/1990 |
| JP | H0388869 A | 4/1991 |
| JP | H1046488 A | 2/1998 |
| JP | H11269201 A | 10/1999 |
| JP | 2006522234 A | 9/2006 |
| WO | 2004088039 A1 | 10/2004 |
| WO | 2020068151 A1 | 4/2020 |

DISPERSIBLE NONWOVEN MATERIALS INCLUDING CMC-BASED BINDERS

CROSS-REFERENCE TO RELATED APPLICATIONS

This is a national stage application that claims the benefit of the filing date and disclose of International Application PCT/IB2020/057398, filed on Aug. 5, 2020, which is related to and claims the benefit of the filing date and disclosures under U.S. Provisional Application No. 62/884,236 filed on Aug. 8, 2019, the contents of which are incorporated by reference herein.

1. FIELD OF THE INVENTION

Dispersible nonwoven materials bonded with a carboxymethyl cellulose (CMC)-based binder including a metallic salt are provided. Such nonwoven materials can be used for a variety of applications and can have improved wet strength and dispersibility.

2. BACKGROUND OF THE INVENTION

Dispersible nonwoven products, such as wipes, are widely used and provide for relatively inexpensive, sanitary, and convenient use in numerous applications. Several attempts have been made to produce flushable and dispersible products that are sufficiently strong enough for their intended purpose, and yet adequately disposable.

One such approach is the incorporation of water-soluble or redispersible polymeric binders to create pre-moistened wipes. Technical problems associated with pre-moistened wipes and tissues using such binders include providing sufficient binder in the nonwoven material to provide the necessary dry and wet tensile strength for use in its intended application, while at the same time protecting the dispersible binder from dissolving due to the aqueous environment during storage. Further, while having the necessary dry and wet tensile strength, the wipe material also needs to be readily dispersible for proper disposal.

Such water-soluble binders are disclosed, for example, in U.S. Pat. No. 5,281,306 to Kakiuchi et al. Kakiuchi et al. provides a water-soluble binder having a carboxyl group, at least one metallic ion, and an aqueous cleaning agent containing an organic solvent to provide dispersible materials. However, there continues remain a need for improved binder applications which provide for simultaneous and acceptable strength and dispersibility in nonwoven materials. The disclosed subject matter addresses these and other needs.

3. SUMMARY

The presently disclosed subject matter provides nonwoven materials which are at least partially coated with a carboxymethyl cellulose (CMC)-based binder including a metallic salt. It was surprisingly and advantageously found that binders of the present disclosure at a pH of from about 4.3 to about 4.5 provided nonwoven materials with both high wet strength and rapid dispersibility.

The present disclosure provides nonwoven materials. The nonwoven materials can include at least one layer comprising cellulose fibers, synthetic fibers, or combinations thereof. The at least one layer can be covered on at least a portion of its surface with a binder. The binder can include carboxymethyl cellulose (CMC) and a metallic salt. The binder can have a pH of from about 4.3 to about 4.5.

In certain embodiments, the binder can have a pH of from about 4.3 to about 4.4 or from about 4.4 to about 4.5.

In certain embodiments, the CMC and the metallic salt can be present in binder in a ratio of about 1:1 or about 3:1.

In certain embodiments, the metallic salt can include calcium chloride.

In certain embodiments, the binder can further include a surfactant.

In certain embodiments, the plasticizer can include polyethylene glycol.

In certain embodiments, the cellulose fibers can include softwood fibers, hardwood fibers, or combinations thereof.

In certain embodiments, the synthetic fibers can include bicomponent fibers.

In certain embodiments, the nonwoven material can have a wet strength of from about 350 gli to about 400 gli.

The present disclosure provides a wipe including the nonwoven material of the present disclosure and a lotion. The present disclosure further provides a personal care product including the nonwoven material of the present disclosure.

The foregoing has outlined broadly the features and technical advantages of the present application in order that the detailed description that follows can be better understood. Additional features and advantages of the application will be described hereinafter which form the subject of the claims of the application. It should be appreciated by those skilled in the art that the conception and specific embodiment disclosed can be readily utilized as a basis for modifying or designing other structures for carrying out the same purposes of the present application. It should also be realized by those skilled in the art that such equivalent constructions do not depart from the spirit and scope of the application as set forth in the appended claims. The novel features which are believed to be characteristic of the application, both as to its organization and method of operation, together with further objects and advantages will be better understood from the following description.

4. BRIEF DESCRIPTION OF THE DRAWINGS

Figure 6A:
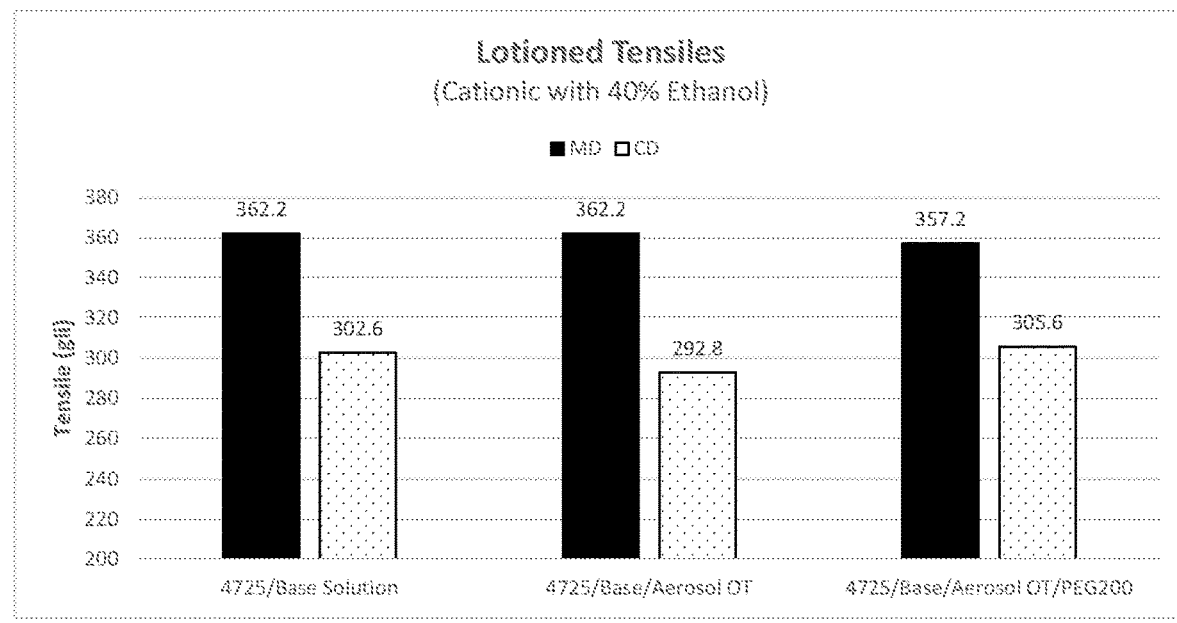
Figure 6B:
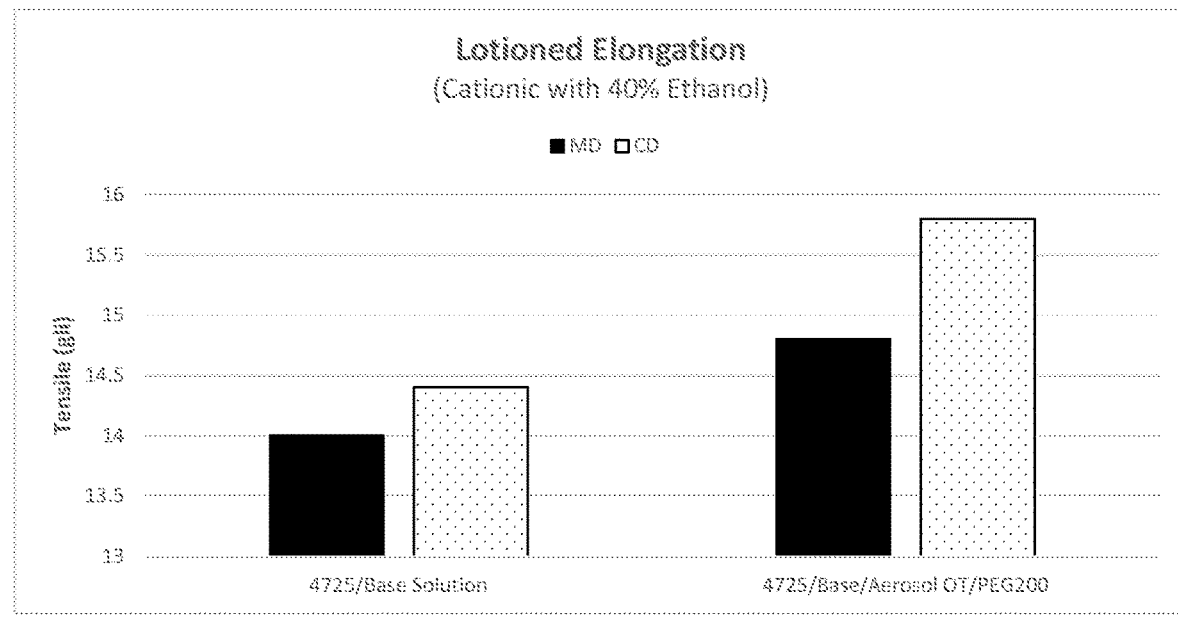

FIG. 6A depicts the wet strength testing results of nonwoven materials including binders optionally prepared with surfactants and plasticizers in accordance with certain non-limiting embodiments as provided in Example 6; and FIG. 6B depicts the wet strength testing results of nonwoven materials including binders optionally prepared with surfactants and plasticizers in accordance with certain non-limiting embodiments as provided in Example 6.

5. DETAILED DESCRIPTION

The presently disclosed subject matter provides for nonwoven materials comprising at least one layer of cellulose fibers, synthetic fibers, or combinations thereof. The nonwoven materials are at least partially coated with a binder comprising carboxymethyl cellulose (CMC) and a metallic salt. Binders of the present disclosure can be applied to the nonwoven material at a pH of from about 4.3 to about 4.5. Such nonwoven materials including binders of the present disclosure can simultaneously have improved wet strength and dispersibility. The presently disclosed subject matter also provides methods for making such materials. These and other aspects of the disclosed subject matter are discussed more in the detailed description and examples.

Definitions

The terms used in this specification generally have their ordinary meanings in the art, within the context of this subject matter and in the specific context where each term is used. Certain terms are defined below to provide additional guidance in describing the compositions and methods of the disclosed subject matter and how to make and use them.

As used in the specification and the appended claims, the singular forms "a," "an" and "the" include plural referents unless the context clearly dictates otherwise. Thus, for example, reference to "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to systems or processes, the term can mean within an order of magnitude, preferably within 5-fold, and more preferably within 2-fold, of a value.

The term "basis weight" as used herein refers to the quantity by weight of a compound over a given area. Examples of the units of measure include grams per square meter as identified by the acronym "gsm".

As used herein, the term "cellulose" or "cellulosic" includes any material having cellulose as a major constituent, and specifically, comprising at least 50 percent by weight cellulose or a cellulose derivative. Thus, the term includes cotton, typical wood pulps, cellulose acetate, rayon, thermochemical wood pulp, chemical wood pulp, debonded chemical wood pulp, milkweed floss, microcrystalline cellulose, microfibrillated cellulose, and the like.

As used herein, the phrase "chemically modified," when used in reference to a fiber, means that the fiber has been treated with a polyvalent metal-containing compound to produce a fiber with a polyvalent metal-containing compound bound to it. It is not necessary that the compound chemically bond with the fibers, although it is preferred that the compound remain associated in close proximity with the fibers, by coating, adhering, precipitation, or any other mechanism such that it is not dislodged from the fibers during normal handling of the fibers. In particular, the compound can remain associated with the fibers even when wetted or washed with a liquid. For convenience, the association between the fiber and the compound can be referred to as the bond, and the compound can be said to be bound to the fiber.

As used herein, the term "fiber" or "fibrous" refers to a particulate material wherein the length to diameter ratio of such particulate material is greater than about 10. Conversely, a "nonfiber" or "nonfibrous" material is meant to refer to a particulate material wherein the length to diameter ratio of such particulate matter is about 10 or less.

As used herein, a "nonwoven" refers to a class of material, including but not limited to textiles or plastics. Nonwovens are sheet or web structures made of fiber, filaments, molten plastic, or plastic films bonded together mechanically, thermally, or chemically. A nonwoven is a fabric made directly from a web of fiber, without the yarn preparation necessary for weaving or knitting. In a nonwoven, the assembly of fibers is held together by one or more of the following: (1) by mechanical interlocking in a random web or mat; (2) by fusing of the fibers; or (3) by bonding with a cementing medium such as a natural or synthetic resin or binder.

As used herein, the term "weight percent" is meant to refer to either (i) the quantity by weight of a constituent/component in the material as a percentage of the weight of a layer of the material; or (ii) to the quantity by weight of a constituent/component in the material as a percentage of the weight of the final microfiber wipe material or product.

Fibers

The nonwoven material of the presently disclosed subject matter comprises fibers. The fibers can be natural, synthetic, or a mixture thereof. In certain embodiments, the fibers can be cellulose-based fibers, one or more synthetic fibers, or a mixture thereof. In certain embodiments, nonwoven materials of the present disclosure can include layers of different cellulose fibers. In certain embodiments, different cellulose fibers can be blended together in one or more layers of the nonwoven material.

Cellulose Fibers

Any cellulose fibers known in the art, including cellulose fibers of any natural origin, such as those derived from wood pulp or regenerated cellulose, can be used in a cellulosic layer. In certain embodiments, cellulose fibers include, but are not limited to, digested fibers, such as kraft, prehydrolyzed kraft, soda, sulfite, chemi-thermal mechanical, and thermo-mechanical treated fibers, derived from softwood, hardwood or cotton linters. In other embodiments, cellulose fibers include, but are not limited to, kraft digested fibers, including prehydrolyzed kraft digested fibers. Non-limiting examples of cellulose fibers suitable for use in this subject matter are the cellulose fibers derived from softwoods, such as pines, firs, and spruces. Other suitable cellulose fibers include, but are not limited to, those derived from Esparto grass, bagasse, kemp, flax, hemp, kenaf, and other lignaceous and cellulosic fiber sources. Suitable cellulose fibers include, but are not limited to, bleached Kraft southern pine fibers sold under the trademark FOLEY FLUFFS® (Buckeye Technologies Inc., Memphis, Tenn.). Additionally, fibers sold under the trademark CELLU TISSUE® (e.g., Grade 3024) (Clearwater Paper Corporation, Spokane, Wash.) are utilized in certain aspects of the disclosed subject matter.

The nonwoven materials of the disclosed subject matter can also include, but are not limited to, a commercially available bright fluff pulp including, but not limited to, southern softwood kraft (such as Golden Isles® 4725 from GP Cellulose) or southern softwood fluff pulp (such as Treated FOLEY FLUFFS®) northern softwood sulfite pulp (such as T 730 from Weyerhaeuser), or hardwood pulp (such as Eucalyptus). In certain embodiments, the nonwoven materials can include Eucalyptus fibers (Suzano, untreated). While certain pulps can be preferred based on a variety of factors, any absorbent fluff pulp or mixtures thereof can be used. In certain embodiments, wood cellulose, cotton linter pulp, chemically modified cellulose such as crosslinked cellulose fibers and highly purified cellulose fibers can be used. Non-limiting examples of additional pulps are FOLEY FLUFFS® FFTAS (also known as FFTAS or Buckeye Technologies FFT-AS pulp), and Weyco CF401.

In certain embodiments, fine fibers, such as certain softwood fibers can be used. Certain non-limiting examples of such fine fibers, with pulp fiber coarseness properties are provided in Table I below with reference to Watson, P., et al., Canadian Pulp Fibre Morphology: Superiority and Considerations for End Use Potential, The Forestry Chronicle, Vol. 85 No. 3, 401-408 May/June 2009.

TABLE I

| Softwood Fibers | |
| --- | --- |
| Species | Pulp Fiber Coarseness (mg/100 m) |
| Coastal Douglas-fir | 24 |
| Western hemlock | 20 |
| Spruce/pine | 18 |
| Western redcedar | 16 |
| Southern pine | 30 |
| Radiata pine | 22 |
| Scandinavian pine | 20 |
| Black spruce | 18 |

In certain embodiments, fine fibers, such as certain hardwood fibers can be used. Certain non-limiting examples of such fine fibers, with pulp fiber coarseness properties are provided in Table II with reference, at least in part, to Horn, R., Morphology of Pulp Fiber from Hardwoods and Influence on Paper Strength, Research Paper FPL 312, Forest Products Laboratory, U.S. Department of Agriculture (1978) and Bleached Eucalyptus Kraft Pulp ECF Technical Sheet (April 2017) (available at: https://www.metsafibre.com/en/Documents/Data-sheets/Cenibra-euca-Eucalyptus.pdf). In particular embodiments, Eucalyptus pulp can be used.

TABLE II

| Hardwood Fibers | |
| --- | --- |
| Species | Pulp Fiber Coarseness (mg/100 m) |
| Red alder | 12.38 |
| Aspen | 8.59 |
| American elm | 9.53 |
| Paper birch | 13.08 |
| American beech | 13.10 |
| Shagbark hickory | 10.59 |
| Sugar maple | 7.86 |
| White oak | 14.08 |
| Eucalyptus | 6.5 +/− 2.3 |

In particular embodiments of the disclosed subject matter, the following cellulose is used: GP4723, a fully treated pulp (Leaf River) (available from Georgia-Pacific); GP4725, a semi-treated pulp (available from Georgia-Pacific); Tencel (available from Lenzing); cellulose flax fibers; Danufil (available from Kelheim); Viloft (available from Kelheim); GP4865, an odor control semi-treated pulp (available from Georgia-Pacific); Grade 3024 Cellu Tissue (available from Clearwater); Brawny Industrial Flax 500 (available from Georgia-Pacific). Nonwoven materials of the present disclosure can include cellulose fibers. In certain embodiments, one or more layers of the nonwoven material can contain from about 5 gsm to about 150 gsm, from about 5 gsm to about 100 gsm, or about from 10 gsm to about 50 gsm cellulose fibers. In particular embodiments, one or more layers can contain about 60 gsm, about 65 gsm, or about 70 gsm cellulose fibers.

Chemically Modified Cellulose Fibers

The presently disclosed subject matter contemplates the use of cellulose-based fibers that are chemically modified. As embodied herein, the cellulose fibers can be chemically treated with a compound comprising a polyvalent metal ion, e.g., a polyvalent cation. Such chemically modified fibers are described, for the purpose of illustration and not limitation, in U.S. Pat. Nos. 6,562,743 and 8,946,100, the contents of which are hereby incorporated by reference in their entireties. The chemically modified cellulose fibers can optionally be associated with a weak acid. For example, suitable modified cellulose fibers include aluminum-modified FFLE+ fibers from GP Cellulose or Valance from International Paper.

The chemically modified cellulose fiber can be treated with from about 0.1 weight percent to about 20 weight percent of the polyvalent cation-containing compound, based on the dry weight of the untreated fiber, desirably with from about 2 weight percent to about 12 weight percent of the polyvalent metal-containing compound, and alternatively with from about 3 weight percent to about 8 weight percent of the polyvalent cation-containing compound, based on the dry weight of the untreated fiber.

Any polyvalent metal salt including transition metal salts can be used, provided that the compound is capable of increasing the stability of the cellulose fiber in an alkaline environment. Examples of suitable polyvalent metals include beryllium, magnesium, calcium, strontium, barium, titanium, zirconium, vanadium, chromium, molybdenum, tungsten, manganese, iron, cobalt, nickel, copper, zinc, aluminum and tin. In certain embodiments, the ions include aluminum, iron and tin. In certain embodiments, the metal ions have oxidation states of +3 or +4. In certain embodiments, the polyvalent metal is aluminum. Any salt containing the polyvalent metal ion can be employed. Examples of suitable inorganic salts of the above metals include chlorides, nitrates, sulfates, borates, bromides, iodides, fluorides, nitrides, perchlorates, phosphates, hydroxides, sulfides, carbonates, bicarbonates, oxides, alkoxides phenoxides, phosphites, and hypophosphites. Examples of suitable organic salts of the above metals include formates, acetates, butyrates, hexanoates, adipates, citrates, lactates, oxalates, propionates, salicylates, glycinates, tartrates, glycolates, sulfonates, phosphonates, glutamates, octanoates, benzoates, gluconates, maleates, succinates, and 4,5-dihydroxybenzene-1,3-disulfonates. In addition to the polyvalent metal salts, other compounds such as complexes of the above salts include amines, ethylenediaminetetra-acetic acid (EDTA), diethylenetriaminepenta-acetic acid (DIPA), nitrilotri-acetic acid (NTA), 2,4-pentanedione, and ammonia can be used. In certain embodiments, the polyvalent metal salt is aluminum chloride, aluminum hydroxide, or aluminum sulfate. Alum is an aluminum sulfate salt which is soluble in water. In an aqueous slurry of cellulose, some of the alum will penetrate the fiber cell wall, but since the concentration of ions is low, most of the dissolved aluminum salt will be outside the fiber. When the pH is adjusted to precipitate aluminum hydroxide, most of the precipitate adheres to the fiber surface.

In certain embodiments, the chemically modified cellulose fiber has an acid bound or otherwise associated with it. A variety of suitable acids can be employed. In certain embodiments, the acid has a low volatility. In certain embodiments, the acid is a weak acid. For example, and not limitation, suitable acids include inorganic acids such as sodium bisulfate, sodium dihydrogen phosphate and disodium hydrogen phosphate, and organic acids such as formic, acetic, aspartic, propionic, butyric, hexanoic, benzoic, gluconic, oxalic, malonic, succinic, glutaric, tartaric, maleic, malic, phthallic, sulfonic, phosphonic, salicylic, glycolic, citric, butanetetracarboxylic acid (BTCA), octanoic, polyacrylic, polysulfonic, polymaleic, and lignosulfonic acids, as well as hydrolyzed-polyacrylamide and CMC (carboxymethylcellulose). Among the carboxylic acids, acids with two carboxyl groups are preferred, and acids with three carboxyl groups are more preferred. In certain embodiments, the acid is citric acid.

In general, the amount of acid employed can depend on the acidity and the molecular weight of the acid. In certain embodiments, the acid comprises from about 0.5 weight percent of the fibers to about 10 weight percent of the fibers. As used herein, the "weight percent of the fibers" refers to the weight percent of dry fiber treated with the polyvalent metal containing compound, i.e., based on the dry weight of the treated fibers. For example, in certain embodiments, the acid is citric acid in an amount of from about 0.5 weight percent to about 3 weight percent of the fibers. An alternative combination is an aluminum-containing compound and citric acid. For the chemically treated fibers of this aspect of the present disclosure, it is desirable that the weak acid content of the chemically treated fibers is from about 0.5 weight percent to about 10 weight percent based on the dry weight of the treated fibers, more desirably, from about 0.5 weight percent to about 5 weight percent based on the dry weight of the treated fibers, or from about 0.5 weight percent to about 3 weight percent based on the dry weight of the treated fibers.

Alternatively, in certain embodiments, a buffer salt can be used instead of a weak acid in combination with the polyvalent metal-containing compound. Any buffer salt that in water would provide a solution having a pH of less than about 7 is suitable. For example, and not limitation, suitable buffer salts include sodium acetate, sodium oxalate, sodium tartrate, sodium phthalate, sodium dihydrogen phosphate, disodium hydrogen phosphate and sodium borate. Buffer salts can be used in combination with their acids in a combination that in water would provide a solution having a pH of less than about 7, for example, oxalic acid/sodium oxalate, tartaric acid/sodium tartrate, sodium phthalate/phthalic acid, and sodium dihydrogen phosphate/disodium hydrogen phosphate.

In a further variations, the polyvalent metal-containing compound can be used in combination with an insoluble metal hydroxide, such as, for example, magnesium hydroxide, or in combination with one or more alkali stable anti-oxidant chemicals or alkali stable reducing agents that would inhibit fiber degradation in an alkaline oxygen environment. Examples include inorganic chemicals such as sodium sulfite, and organic chemicals such as hydroquinone.

For the chemically modified cellulose fibers, it is desirable that the buffer salt content, the buffer salt weak acid combination content, the insoluble metal hydroxide content and/or the antioxidant content of the chemically treated fibers is from about 0.5 weight percent to about 10 weight percent based on the dry weight of the treated fibers, more desirably, from about 0.5 weight percent to about 5 weight percent based on the dry weight of the treated fibers, or from about 0.5 weight percent to about 3 weight percent based on the dry weight of the treated fibers.

In certain embodiments, reducing agents can be applied to the modified cellulose fibers to maintain desired levels of fiber brightness, by reducing brightness reversion. The addition of acidic substances can cause browning of fibers when heated during processing of webs containing the fibers. Reducing agents counter the browning of the fibers. The reducing agent can also bond to the fibers. Suitable reducing agents include sodium hypophosphite, sodium bisulfite, and mixtures thereof.

The fibers suitable for use in the practice of the present disclosure can be treated in a variety of ways to provide the polyvalent metal ion-containing compound in close association with the fibers. In certain embodiments, the compound is introduced in solution with the fibers in slurry form and cause the compound to precipitate onto the surface of the fibers. Alternatively, the fibers can be sprayed with the compound in aqueous or non-aqueous solution or suspension. The fibers can be treated while in an individualized state, or in the form of a web. For example, the compound can be applied directly onto the fibers in powder or other physical form. Whatever method is used, however, it is preferred that the compound remain bound to the fibers, such that the compound is not dislodged during normal physical handling of the fiber before contact of the fiber with liquid.

In certain embodiments, the treated fibers of the present disclosure are made from cellulose fiber known as FOLEY FLUFFS® from GP Cellulose. The pulp is slurried, the pH is adjusted to about 4.0, and aluminum sulfate ($Al_2(SO_4)_3$) in aqueous solution is added to the slurry. The slurry is stirred and the consistency reduced. Under agitation, the pH of the slurry is increased to approximately 5.7. The fibers are then formed into a web or sheet, dried, and, optionally, sprayed with a solution of citric acid at a loading of about 2.5 weight percent of the fibers. The web is then packaged and shipped to end users for further processing, including fiberization to form individualized fibers useful in the manufacture of various products.

In another embodiment, the treated fibers of the present disclosure are made from cellulose fiber obtained from GP Cellulose. The pulp is slurried, the pH is adjusted to about 4.0, and aluminum sulfate ($Al_2(SO_4)_3$) in aqueous solution is added to the slurry. The slurry is stirred and the consistency reduced. Under agitation, the pH of the slurry is increased to approximately 5.7. The fibers are then formed into a web or sheet, dried, and sprayed with a solution of sodium oleate at a loading of about 1.0 weight percent of the fibers. The web is then packaged and shipped to end users for further processing, including re-slurrying to form a web useful in the manufacture of filtration products. If a reducing agent is to be applied, it can applied before a drying step and following any other application steps. The reducing agent can be applied by spraying, painting or foaming.

Metal ion content, including aluminum or iron content, in pulp samples can be determined by wet ashing (oxidizing) the sample with nitric and perchloric acids in a digestion apparatus. A blank is oxidized and carried through the same steps as the sample. The sample is then analyzed using an inductively coupled plasma spectrophotometer, such as, for example, a Perkin-Elmer ICP 6500. From the analysis, the ion content in the sample can be determined in parts per million. The polyvalent cation content desirably is from about 0.1 weight percent to about 5.0 weight percent, based on the dry weight of the treated fibers, more desirably, from about 0.1 weight percent to about 3.0 weight percent, based on the dry weight of the treated fibers, or from about 0.1 weight percent to about 1.5 weight percent, based on the dry weight of the treated fibers, or from about 0.2 weight percent to about 0.9 weight percent, based on the dry weight of the treated fibers, or from about 0.3 weight percent to about 0.8 weight percent, based on the dry weight of the treated fibers.

Without intending to be bound by theory, it is believed that by this process, the soluble $Al_2(SO_4)_3$ introduced to the pulp slurry is converted to insoluble $Al(OH)_3$ as the pH is increased. The insoluble aluminum hydroxide precipitates onto the fiber. Thus, the resultant chemically treated cellulose fibers are coated with $Al(OH)_3$ or contain the insoluble metal within the fiber interior.

The sodium oleate sprayed onto the web containing the fibers dries on the fibers. When the $Al(OH)_3$-oleate treated fibers are formed into a filter based sheet, the aluminum and oleate ions create a hydrophobic environment in addition to increasing the wet strength of the structure. These results are exemplified in the procedures set forth below.

In another embodiment, hydrated aluminum sulfate and sodium oleate are sprayed on the fiber after the drying section of a paper machine. In another embodiment, hydrated aluminum sulfate and sodium oleate are precipitated onto the fiber in the wet end section of a paper machine. In another embodiment, hydrated aluminum sulfate and sodium hypophosphite are sprayed on the fiber prior to the pressing stage, and sodium oleate is sprayed after drying. In another embodiment, hydrated aluminum sulfate, sodium hypophosphite and sodium oleate are sprayed on the fiber prior to the pressing stage. In yet another embodiment, hydrated aluminum sulfate is precipitated onto the fiber, hydrated aluminum and sodium hypophosphite are sprayed on the fiber prior to pressing, and sodium oleate is sprayed on the fiber after drying. In another embodiment, hydrated aluminum sulfate is precipitated onto the fiber and sodium oleate is sprayed on the fiber prior to the pressing stage.

Various materials, structures and manufacturing processes can be used in connection with the presently disclosed modified cellulose fibers, for example and not limitation, as described in U.S. Pat. Nos. 6,241,713, 6,353,148, 6,353,148, 6,171,441, 6,159,335, 5,695,486, 6,344,109, 5,068,079, 5,492,759, 5,269,049, 5,601,921, 5,693,162, 5,922,163, 6,007,653, 6,355,079, 6,403,857, 6,479,415, 6,562,742, 6,562,743, 6,559,081, 6,495,734, 6,420,626, and 8,946,100, and in U.S. Patent Publication Nos. US2004/0208175 and US2002/0013560, all of which are hereby incorporated by reference in their entireties.

In certain embodiments, chemically modified cellulose such as cross-linked cellulose fibers and highly purified cellulose fibers can be used. In particular embodiments, the modified cellulose fibers are crosslinked cellulose fibers. In certain embodiments, the modified cellulose fibers comprise a polyhydroxy compound. Non-limiting examples of polyhydroxy compounds include glycerol, trimethylolpropane, pentaerythritol, polyvinyl alcohol, partially hydrolyzed polyvinyl acetate, and fully hydrolyzed polyvinyl acetate.

In certain embodiments, the modified cellulose pulp fibers have been softened or plasticized to be inherently more compressible than unmodified pulp fibers. The same pressure applied to a plasticized pulp web will result in higher density than when applied to an unmodified pulp web. Additionally, the densified web of plasticized cellulose fibers is inherently softer than a similar density web of unmodified fiber of the same wood type. Softwood pulps can be made more compressible using cationic surfactants as debonders to disrupt interfiber associations. Use of one or more debonders facilitates the disintegration of the pulp sheet into fluff in the airlaid process. Examples of debonders include, but are not limited to, those disclosed in U.S. Pat. Nos. 4,432,833, 4,425,186 and 5,776,308, all of which are hereby incorporated by reference in their entireties. One example of a debonder-treated cellulose pulp is FFLE+. Plasticizers for cellulose, which can be added to a pulp slurry prior to forming wetlaid sheets, can also be used to soften pulp, although they act by a different mechanism than debonding agents. Plasticizing agents act within the fiber, at the cellulose molecule, to make flexible or soften amorphous regions. The resulting fibers are characterized as limp. Since the plasticized fibers lack stiffness, the comminuted pulp is easier to densify compared to fibers not treated with plasticizers. Plasticizers include, but are not limited to, polyhydric alcohols such as glycerol, low molecular weight polyglycol such as polyethylene glycols, and polyhydroxy compounds. These and other plasticizers are described and exemplified in U.S. Pat. Nos. 4,098,996, 5,547,541 and 4,731,269, all of which are hereby incorporated by reference in their entireties. Ammonia, urea, and alkylamines are also known to plasticize wood products, which mainly contain cellulose (A. J. Stamm, Forest Products Journal 5(6):413, 1955, hereby incorporated by reference in its entirety).

Nonwoven materials of the present disclosure can include modified cellulose fibers. In certain embodiments, one or more layers of the nonwoven material can contain from about 5 gsm to about 150 gsm, from about 5 gsm to about 100 gsm, or from about 10 gsm to about 50 gsm modified cellulose fibers. In particular embodiments, one or more layers can contain about 60 gsm, about 65 gsm, or about 70 gsm modified cellulose fibers.

Synthetic Fibers

In addition to the use of cellulose fibers, the presently disclosed subject matter also contemplates the use of synthetic fibers. In one embodiment, the synthetic fibers comprise mono-component fibers.

Monofilament fibers are typically fabricated commercially by melt spinning. In this procedure, each molten polymer is extruded through a die, for example, a spinneret, with subsequent pulling of the molten polymer to move it away from the face of the spinneret. This is followed by solidification of the polymer by heat transfer to a surrounding fluid medium, for example chilled air, and taking up of the now solid filament. Non-limiting examples of additional steps after melt spinning can also include hot or cold drawing, heat treating, crimping and cutting. This overall manufacturing process is generally carried out as a discontinuous two-step process that first involves spinning of the filaments and their collection into a tow that comprises numerous filaments. During the spinning step, when molten polymer is pulled away from the face of the spinneret, some drawing of the filament does occur which can also be called the draw-down. This is followed by a second step where the spun fibers are drawn or stretched to increase molecular alignment and crystallinity and to give enhanced strength and other physical properties to the individual filaments. Subsequent steps can include, but are not limited to, heat setting, crimping and cutting of the filament into fibers.

Monofilament fibers can also be formed in a continuous process where the spinning and drawing are done in a continuous process. During the fiber manufacturing process it is desirable to add various materials to the fiber after the melt spinning step at various subsequent steps in the process. These materials can be referred to as "finish" and be comprised of active agents such as, but not limited to, lubricants and anti-static agents. The finish is typically delivered via an aqueous based solution or emulsion. Finishes can provide desirable properties for both the manufacturing of the fiber and for the user of the fiber, for example in an airlaid or wetlaid process.

Numerous other processes are involved before, during and after the spinning and drawing steps and are disclosed in U.S. Pat. Nos. 4,950,541, 5,082,899, 5,126,199, 5,372,885, 5,456,982, 5,705,565, 2,861,319, 2,931,091, 2,989,798, 3,038,235, 3,081,490, 3,117,362, 3,121,254, 3,188,689, 3,237,245, 3,249,669, 3,457,342, 3,466,703, 3,469,279, 3,500,498, 3,585,685, 3,163,170, 3,692,423, 3,716,317, 3,778,208, 3,787,162, 3,814,561, 3,963,406, 3,992,499, 4,052,146, 4,251,200, 4,350,006, 4,370,114, 4,406,850, 4,445,833, 4,717,325, 4,743,189, 5,162,074, 5,256,050, 5,505,889, 5,582,913, and 6,670,035, all of which are hereby incorporated by reference in their entireties.

The presently disclosed subject matter can also include, but are not limited to, articles that contain monofilament fibers that are partially drawn with varying degrees of draw or stretch, highly drawn fibers and mixtures thereof. The use of both partially drawn and highly drawn fibers in the same structure can be leveraged to meet specific physical and performance properties based on how they are incorporated into the structure.

The fibers of the presently disclosed subject matter are not limited in scope to any specific polymers as any partially drawn fiber can provide enhanced performance regarding elongation and strength. The degree to which the partially drawn fibers are drawn is not limited in scope as different degrees of drawing will yield different enhancements in performance. The scope of this subject matter covers the use of partially drawn homopolymers such as polyester, polypropylene, nylon, and other melt spinnable polymers. Nonwoven materials of the present disclosure can include monofilament fibers. In certain embodiments, one or more layers of the nonwoven material can contain from about 5 gsm to about 150 gsm, from about 5 gsm to about 100 gsm, or from about 10 gsm to about 50 gsm monofilament fibers. In particular embodiments, one or more layers can contain about 60 gsm, about 65 gsm, or about 70 gsm monofilament fibers.

In particular embodiments, the monofilament fibers are low dtex staple monofilament fibers in the range of about 0.5 dtex to about 20 dtex. In certain embodiments, the dtex value can range from about 1.3 dtex to about 15 dtex, from about 1.5 dtex to about 10 dtex, from about 1.7 dtex to about 6.7 dtex, or from about 2.2 dtex to about 5.7 dtex. In certain embodiments, the dtex value is 1.3 dtex, 1.5 dtex, 1.7 dtex, 2.2 dtex, 3.3 dtex, 5.7 dtex, 6.7 dtex, or 10 dtex.

Other synthetic fibers suitable for use in various embodiments as fibers include, but are not limited to, fibers made from various polymers including, by way of example and not by limitation, acrylic, polyamides (including, but not limited to, Nylon 6, Nylon 6/6, Nylon 12, polyaspartic acid, polyglutamic acid), polyamines, polyimides, polyacrylics (including, but not limited to, polyacrylamide, polyacrylonitrile, esters of methacrylic acid and acrylic acid), polycarbonates (including, but not limited to, polybisphenol A carbonate, polypropylene carbonate), polydienes (including, but not limited to, polybutadiene, polyisoprene, polynorbornene), polyepoxides, polyesters (including, but not limited to, polyethylene terephthalate, polybutylene terephthalate, polytrimethylene terephthalate, polycaprolactone, polyglycolide, polylactide, polyhydroxybutyrate, polyhydroxyvalerate, polyethylene adipate, polybutylene adipate, polypropylene succinate), polyethers (including, but not limited to, polyethylene glycol (polyethylene oxide), polybutylene glycol, polypropylene oxide, polyoxymethylene (paraformaldehyde), polytetramethylene ether (polytetrahydrofuran), polyepichlorohydrin), polyfluorocarbons, formaldehyde polymers (including, but not limited to, urea-formaldehyde, melamine-formaldehyde, phenol formaldehyde), natural polymers (including, but not limited to, cellulosics, chitosans, lignins, waxes), polyolefins (including, but not limited to, polyethylene, polypropylene, polybutylene, polybutene, polyoctene), polyphenylenes (including, but not limited to, polyphenylene oxide, polyphenylene sulfide, polyphenylene ether sulfone), silicon containing polymers (including, but not limited to, polydimethyl siloxane, polycarbomethyl silane), polyurethanes, polyvinyls (including, but not limited to, polyvinyl butyral, polyvinyl alcohol, esters and ethers of polyvinyl alcohol, polyvinyl acetate, polystyrene, polymethylstyrene, polyvinyl chloride, polyvinyl pyrrolidone, polymethyl vinyl ether, polyethyl vinyl ether, polyvinyl methyl ketone), polyacetals, polyarylates, and copolymers (including, but not limited to, polyethylene-co-vinyl acetate, polyethylene-co-acrylic acid, polybutylene terephthalate-co-polyethylene terephthalate, polylauryllactam-block-polytetrahydrofuran), polybutylene succinate and polylactic acid based polymers.

In other specific embodiments, the synthetic layer contains synthetic filaments. The synthetic filaments can be formed by spinning and/or extrusion processes. For example, such processes can be similar to the methods described above with reference to melt spinning processes. The synthetic filaments can include one or more continuous strands. In certain embodiments, the synthetic filaments can include polypropylene.

Binders

The nonwoven materials of the present disclosure can include a binder. In certain embodiments, the nonwoven material can be coated on at least an outer surface with a binder. Such binders can include carboxymethyl cellulose (CMC) and one or more metal salts, for example, calcium chloride. In certain embodiments, such binders can include CMC, one or more metallic salts, one or more surfactants, and one or more plasticizers. In particular embodiments, the binder can have a pH of from about 4.3 to about 4.5.

Suitable binders include, but are not limited to, liquid binders and powder binders. Non-limiting examples of liquid binders include emulsions, solutions, or suspensions of binders. Non-limiting examples of binders include polyethylene powders, copolymer binders, vinylacetate ethylene binders, styrene-butadiene binders, urethanes, urethane-based binders, acrylic binders, thermoplastic binders, natural polymer based binders, and mixtures thereof.

Carboxymethyl Cellulose (CMC)

In certain embodiments, the binder can be salt sensitive and water-soluble. The binder can include a carboxymethyl cellulose (CMC) polymer. In particular embodiments, the binder can include sodium CMC or calcium CMC. The binder can further include temporary wet strength agents including, but not limited to Diallyldimethylammonium Chloride (DADMAC), Polydiallyldimethylammonium chloride (polyDADMAC), N-methylolacrylamide (NMA), polyacrylamide (PAM), glyoxylated polyacrylamide (GPAM), polyamide epichlorohydrin (PAE), polyamidoamine epichlorohydrin (PAAE) or combinations thereof. Other binders can include sodium CMC cross-linked with carboxylic acid, cationic ion sensitive binder, or a soluble starch. Any water-soluble binder that is not significantly soluble in the miscible solution with reduced polarity should increase strength, dispersibility, and shape retention are suitable for use with the nonwoven materials of the present disclosure.

In certain embodiments, the binder is a cellulosic binder, for example, CMC. In certain embodiments, the CMC polymer can be anionic and water-soluble. In particular embodiments, the carboxymethyl cellulose (CMC) can be Hercules Aqualon CMC (Ashland, Inc., Covington, KY) or Blanose 7L1C1 (Ashland, Inc., Covington, KY). In certain embodiments, the nonwoven materials of the present disclosure can include from about 2% to about 15%, from about 4% to about 12%, or from about 5% to about 10% by weight of carboxymethyl cellulose (CMC), based on a total weight of the nonwoven material. In particular embodiments, the nonwoven materials of the present disclosure can include about 2%, about 5%, about 8%, about 10%, or about 15% by weight of carboxymethyl cellulose (CMC), based on a total weight of the nonwoven material.

Metal Salts

In certain embodiments, the binder can include one or more metal salts. Any polyvalent metal salt including transition metal salts can be used. Non-limiting examples of suitable polyvalent metals include beryllium, magnesium, calcium, strontium, barium, titanium, zirconium, vanadium, chromium, molybdenum, tungsten, manganese, iron, cobalt, nickel, copper, zinc, aluminum and tin. In certain embodiments, the ions include aluminum, iron and tin. In certain embodiments, the metal ions have oxidation states of +3 or +4. Any salt containing the polyvalent metal ion can be employed. Non-limiting examples of examples of suitable inorganic salts of the above metals include chlorides, nitrates, sulfates, borates, bromides, iodides, fluorides, nitrides, perchlorates, phosphates, hydroxides, sulfides, carbonates, bicarbonates, oxides, alkoxides phenoxides, phosphites, and hypophosphites. Non-limiting examples of examples of suitable organic salts of the above metals include formates, acetates, butyrates, hexanoates, adipates, citrates, lactates, oxalates, propionates, salicylates, glycinates, tartrates, glycolates, sulfonates, phosphonates, glutamates, octanoates, benzoates, gluconates, maleates, succinates, and 4,5-dihydroxy-benzene-1,3-disulfonates. In addition to the polyvalent metal salts, other compounds such as complexes of the above salts include, but are not limited to, amines, ethylenediaminetetra-acetic acid (EDTA), diethylenetriaminepenta-acetic acid (DIPA), nitrilotri-acetic acid (NTA), 2,4-pentanedione, and ammonia can be used. In particular embodiments, the one or more metal salts can include calcium chloride ($CaCl_2$). In certain embodiments, the binder can include from about 5% to about 35%, from about 10% to about 30%, or from about 15% to about 25% by weight of one or more metal salts, based on a total weight of carboxymethyl cellulose (CMC) binder. In particular embodiments, the nonwoven materials of the present disclosure can include about 10%, about 15%, about 20%, about 25%, or about 30% by weight of one or more metal salts, based on a total weight of carboxymethyl cellulose (CMC) binder.

Surfactants

In certain embodiments, the binder can include one or more surfactants. These binders can have a surfactant incorporated into them during the manufacturing process or can have a surfactant incorporated into them after manufacturing and before application to the web. Such surfactants would include, but would not be limited to, the anionic surfactant Aerosol OT (Cytec Industries, West Paterson, NJ) which can be incorporated at about 0.75% by weight into the binder. In particular embodiments, the one or more surfactants can include Aerosol OT-75 (Cytec Industries, Inc., West Paterson, NJ). In certain embodiments, the nonwoven materials of the present disclosure can include from about 0.5% to about 2.5%, from about 0.75% to about 2.25%, or from about 1% to about 2% by weight of surfactant, based on a total weight of carboxymethyl cellulose (CMC) binder. In particular embodiments, the nonwoven materials of the present disclosure can include about 0.75%, about 1%, about 1.5%, or about 2% of surfactant by weight, based on a total weight of carboxymethyl cellulose (CMC) binder.

Plasticizers

In certain embodiments, the binder can include one or more plasticizers. Plasticizers can include, but are not limited to, polyhydric alcohols such as glycerol; low molecular weight polyglycol such as polyethylene glycols and polyhydroxy compounds. These and other plasticizers are described and exemplified in U.S. Pat. Nos. 4,098,996, 5,547,541 and 4,731,269, all of which are hereby incorporated by reference in their entireties. For example and not limitation, the plasticizer can be polyethylene glycol 100 (PEG 100), polyethylene glycol 200 (PEG 200), polyethylene glycol 300 (PEG 300), or polyethylene glycol 400 (PEG 400). Ammonia, urea, and alkylamines are also known to plasticize wood products, which mainly contain cellulose (A. J. Stamm, Forest Products Journal 5(6):413, 1955, hereby incorporated by reference in its entirety. In particular embodiments, the one or more plasticizers can include PEG 200 (CARBOWAX, Dow Chemical Co.). In certain embodiments, the nonwoven materials of the present disclosure can include from about 0.05% to about 2.5%, from about 0.1% to about 2.0%, or from about 0.5% to about 1.5% by weight of plasticizer, based on a total weight of the nonwoven material. In particular embodiments, the nonwoven materials of the present disclosure can include about 0.05%, about 0.1%, about 0.5%, about 1%, about 1.5%, or about 2.0% by weight of plasticizer, based on the total weight of the nonwoven material.

Binder Solutions

In certain embodiments, the binder can be an aqueous solution. The aqueous solution can include CMC and one or more metal salts. In particular embodiments, the one or more metal salts can include calcium chloride ($CaCl_2$)). In certain embodiments, the binder can be an aqueous solution including CMC, one or more metal salts, and one or more surfactants. The one or more metal salts can include calcium chloride ($CaCl_2$)). The one or more surfactants can include an anionic surfactant, such as Aerosol OT (Cytec Industries, West Paterson, NJ). In certain embodiments, the binder can be an aqueous solution including CMC, one or more metal salts, one or more surfactants, and one or more plasticizers. The one or more metal salts can include calcium chloride ($CaCl_2$)). The one or more surfactants can include an anionic surfactant, such as Aerosol OT (Cytec Industries, West Paterson, NJ). The one or more plasticizers can include polyethylene glycol, for example, polyethylene glycol 200 (PEG 200) (CARBOWAX, Dow Chemical Co.).

In certain embodiments, binders can be applied as emulsions in amounts ranging from about from about 1 gsm to about 15 gsm, from about 2 gsm to about 10 gsm, from about 2 gsm to about 8 gsm, or from about 3 gsm to about 5 gsm. In certain embodiments, the nonwoven materials of the present disclosure can include from about 2% to about 15%, from about 3% to about 10%, or from about 5% to about 8% by weight of binder, based on a total weight of the nonwoven material. In certain embodiments, the nonwoven materials of the present disclosure can include about 3%, about 5%, about 8%, or about 10% by weight of binder, based on a total weight of the nonwoven material. In certain embodiments the binder can be applied to the nonwoven material at an add-on rate of from about 5% to about 25%, from about 10% to about 20%, or from about 10% to about 15%. In particular embodiments, the binder can be applied to the nonwoven material at an add-on rate of about 10%, about 13%, about 14%, or about 15%.

The binder, whether or not part of an emulsion, can be applied to one side of a fibrous layer. In certain embodiments, the binder can be applied to an externally facing layer. Alternatively, binder can be applied to both sides of a layer, in equal or disproportionate amounts.

Binder Features

In certain embodiments, the binder can have a ratio of carboxymethyl cellulose (CMC) to metallic salt of about 1:1 or about 3:1.

In certain embodiments, the binder can have a pH of from about 4.3 to about 4.5, from about 4.3 to about 4.4, or from about 4.4 to about 4.5. In particular embodiments, the binder can have a pH of about 4.3, about 4.35, about 4.37, about 4.39, about 4.4, about 4.45, or about 4.5.

Liquid Additives—Lotions and Alcohols

Nonwoven materials of the present disclosure can be pre-moistened with one or more liquid additives, such as lotions. In certain embodiments, the lotions can further include one or more alcohols.

In certain embodiments, the nonwoven material can include one or more cationic lotions or one or more anionic lotions. In certain embodiments, the one or more cationic lotions can have a pH of from about 5 to about 8, from about 7 to about 8, from about 7.5 to about 8, or about 7.76. In certain embodiments, the one or more anionic lotions can have a pH of from about 8 to about 9, about 8 to about 8.5, or about 8.18. In certain embodiments, the one or more lotions can be applied to the nonwoven material in an amount of about three (3) times or about 3.05 times the weight of the nonwoven material.

In certain embodiments, the nonwoven material can include one or more lotions further including one or more alcohols. In particular embodiments, the one or more alcohols can be Ethanol at about 10%, about 20%, about 24%, about 26%, or about 29%. In particular embodiments, the one or more alcohols can be at least about 26%. In certain embodiments, the one or more lotions including one or more alcohols can have a pH of from about 7 to about 9, about 7 to about 8.5, or about 7 to about 8.

Nonwoven Material

The presently disclosed subject matter provides for nonwoven materials. As embodied herein, the nonwoven material can include at least one layer, at least two layers, at least three layers, or at least four layers. In a particular embodiment, the nonwoven material includes one layer.

As embodied herein, the nonwoven material can be an airlaid material.

In certain embodiments, the nonwoven material can include a single layer comprising cellulose fibers. The layer can further include a second type of cellulose fibers. For example and not limitation, the cellulose fibers can comprise modified cellulose fibers, cellulose fluff, and/or eucalyptus pulp. Alternatively, the cellulose fibers of a layer can comprise only softwood fibers. As a further alternatively, the cellulose fibers of a layer can comprise only modified cellulose fibers.

In certain embodiments, the nonwoven material can include a single layer comprising synthetic fibers, such as monofilament fibers. The layer can further include other types of synthetic fibers. In particular embodiments, the synthetic fibers of a layer can comprise only monofilament fibers.

In certain embodiments, the nonwoven material can have multiple layers. In such embodiments, the nonwoven material can include multiple layers comprising cellulose fibers. Alternatively, the nonwoven material can include multiple layers comprising synthetic fibers. In certain embodiments, the nonwoven material can include layers including cellulose fibers, synthetic fibers, or combinations thereof.

The nonwoven material can be coated on at least of a portion of its outer surface with a binder. It is not necessary that the binder chemically bond with a portion of the layer, although it is preferred that the binder remain associated in close proximity with the layer, by coating, adhering, precipitation, or any other mechanism such that it is not dislodged from the layer during normal handling of the layer. For convenience, the association between the layer and the binder discussed above can be referred to as the bond, and the compound can be said to be bonded to the layer. The binder can be applied in amounts ranging from about 1 gsm to about 15 gsm, from about 2 gsm to about 10 gsm, from about 2 gsm to about 8 gsm, or from about 3 gsm to about 5 gsm.

Overall, the first layer can have a basis weight of from about 25 gsm to about 100 gsm, from about 40 gsm to about 80 gsm, from about 50 gsm to about 75 gsm, or from about 55 gsm to about 65 gsm. In particular embodiments, the first layer can have a basis weight of about 54 gsm.

Methods of Making the Nonwoven Material

A variety of processes can be used to assemble the materials used in the practice of this disclosed subject matter to produce the materials, including but not limited to, traditional dry forming processes such as airlaying and carding or other forming technologies such as spunlace or airlace. Preferably, the materials can be prepared by airlaid processes. Airlaid processes include, but are not limited to, the use of one or more forming heads to deposit raw materials of differing compositions in selected order in the manufacturing process to produce a product with distinct strata. This allows great versatility in the variety of products which can be produced.

In one embodiment, the material is prepared as a continuous airlaid web. The airlaid web is typically prepared by disintegrating or defiberizing a cellulose pulp sheet or sheets, typically by hammermill, to provide individualized fibers. Rather than a pulp sheet of virgin fiber, the hammermills or other disintegrators can be fed with recycled airlaid edge trimmings and off-specification transitional material produced during grade changes and other airlaid production waste. Being able to thereby recycle production waste would contribute to improved economics for the overall process. The individualized fibers from whichever source, virgin or recycled, are then air conveyed to forming heads on the airlaid web-forming machine. A number of manufacturers make airlaid web forming machines suitable for use in the disclosed subject matter, including Dan-Web Forming of Aarhus, Denmark, M&J Fibretech A/S of Horsens, Denmark, Rando Machine Corporation, Macedon, N.Y. which is described in U.S. Pat. No. 3,972,092, Margasa Textile Machinery of Cerdanyola del Valles, Spain, and DOA International of Wels, Austria. While these many forming machines differ in how the fiber is opened and air-conveyed to the forming wire, they all are capable of producing the webs of the presently disclosed subject matter. The Dan-Web forming heads include rotating or agitated perforated drums, which serve to maintain fiber separation until the fibers are pulled by vacuum onto a foraminous forming conveyor or forming wire. In the M&J machine, the forming head is basically a rotary agitator above a screen. The rotary agitator can comprise a series or cluster of rotating propellers or fan blades. Other fibers, are opened, weighed, and mixed in a fiber dosing system such as a textile feeder supplied by Laroche S. A. of Cours-La Ville, France. From the textile feeder, the fibers are air conveyed to the forming heads of the airlaid machine where they are further mixed with the comminuted cellulose pulp fibers from the hammer mills and deposited on the continuously moving forming wire. Where defined layers are desired, separate forming heads can be used for each type of fiber. Alternatively or additionally, one or more layers can be prefabricated prior to being combined with additional layers, if any. In certain embodiments, the forming wire can be patterned, such that at least one layer of the resulting nonwoven material is patterned.

The airlaid web is transferred from the forming wire to a calendar or other densification stage to densify the web, if necessary, to increase its strength and control web thickness. In one embodiment, the fibers of the web are then bonded by passage through an oven set to a temperature high enough to fuse the included thermoplastic or other binder materials. In a further embodiment, secondary binding from the drying or curing of a latex spray or foam application occurs in the same oven. The oven can be a conventional through-air oven, be operated as a convection oven, or can achieve the necessary heating by infrared or even microwave irradiation. In particular embodiments, the airlaid web can be treated with additional additives before or after heat curing. The airlaid web can optionally be embossed or otherwise patterned. Subsequently, the airlaid web can be rolled into bale on a roller.

Applications and Features of the Nonwoven Material

The nonwoven materials of the disclosed subject matter can be used for any application as known in the art. The nonwoven materials can be used alone or as a component in other consumer products. For example, the nonwoven materials can be used either alone or as a component in a variety of articles, including cleaning articles, personal care wipes such as premoistened dispersible wipes, and the like. Such nonwoven materials can have adequate strength and simultaneously be rapidly dispersible in water.

The presently disclosed nonwoven materials can have improved mechanical properties. For example, the nonwoven materials can be incorporated into a wipe, e.g., a wipe that is wetted with a lotion. The nonwoven materials can have a cross-machine direction (CD) wet tensile strength of greater than about 50 gli, greater than about 100 gli, or greater than about 200 gli, or greater than about 250 gli, or greater than about 300 gli, or greater than about 400 gli. In certain embodiments, the nonwoven material can have a cross-machine direction (CD) wet tensile strength of from about 100 gli to about 500 gli, about 150 gli to about 450 gli, or from about 200 gli to about 400 gli. In particular embodiments, the nonwoven material can have a cross-machine direction (CD) wet tensile strength of about 100 gli, about 150 gli, about 200 gli, about 250 gli, about 300 gli, about 400 gli, about 450 gli, or about 500 gli. In certain embodiments, the nonwoven material can have a machine direction (MD) wet tensile strength of greater than about 50 gli, greater than about 100 gli, or greater than about 200 gli, or greater than about 250 gli, or greater than about 300 gli, or greater than about 400 gli. In certain embodiments, the nonwoven material can have a machine direction (MD) wet tensile strength of from about 100 gli to about 500 gli, about 150 gli to about 450 gli, or from about 200 gli to about 400 gli. In particular embodiments, the nonwoven material can have a machine direction (MD) wet tensile strength of about 100 gli, about 150 gli, about 200 gli, about 250 gli, about 300 gli, about 400 gli, about 450 gli, or about 500 gli. Additionally, the nonwoven materials can have a wet elongation at peak load in the cross-machine direction (CD) of greater than about 5%, greater than about 10%, or greater than about 13%, or greater than about 15%, or from about 10% to about 15%. In particular embodiments, the nonwoven materials can have a wet elongation peak load in the cross-machine direction (CD) of about 5%, about 6%, about 8%, about 10%, or about 15%. In certain embodiments, the nonwoven materials can have a wet elongation at peak load in the machine direction (MD) of greater than about 5%, greater than about 10%, or greater than about 13%, or greater than about 15%, or from about 10% to about 15%. In particular embodiments, the nonwoven materials can have a wet elongation peak load in the machine direction (MD) of about 5%, about 6%, about 8%, about 10%, or about 15%.

In certain embodiments, the nonwoven materials can have a cross-machine direction (CD) dry tensile strength of from about 500 gli to about 2500 gli, from about 900 gli to about 2000 gli, or from about 1000 gli to about 1500 gli. In particular embodiments, the nonwoven materials can have a cross-machine direction (CD) dry tensile strength of about 600 gli, about 700 gli, about 800 gli, about 1000 gli, about 1200 gli, or about 1500 gli. In certain embodiments, the nonwoven materials can have a machine direction (MD) dry tensile strength of from about 500 gli to about 2500 gli, from about 900 gli to about 2000 gli, or from about 1000 gli to about 1500 gli. In particular embodiments, the nonwoven materials can have a machine direction (MD) dry tensile strength of about 600 gli, about 700 gli, about 800 gli, about 1000 gli, about 1200 gli, or about 1500 gli. Additionally, the nonwoven materials can have a cross-machine direction (CD) dry elongation of from about 2% to about 15%, about 2% to about 8%, or about 2% to about 5%. In particular embodiments, the nonwoven materials can have a cross-machine direction (CD) dry elongation of about 2%, about 3%, about 4%, about 11%, about 12%, about 13%, or about 14%. In certain embodiments, the nonwoven materials can have a machine direction (MD) dry elongation of from about 2% to about 15%, about 2% to about 8%, or about 2% to about 5%. In particular embodiments, the nonwoven materials can have a cross-machine direction (MD) dry elongation of about 2%, about 3%, about 4%, about 11%, about 12%, about 13%, or about 14%.

The nonwoven materials of the present disclosure can be rapidly dispersible. In certain embodiments, the nonwoven material can disperse in water in less than about 20 seconds, less than about 18 seconds, less than about 15 seconds, less than about 10 seconds, or less than about 5 seconds.

6. EXAMPLES

The following examples are merely illustrative of the presently disclosed subject matter and they should not be considered as limiting the scope of the subject matter in any way.

Example 1: CMC-Bonded Nonwoven Materials (Cellulose)—Wet Strength

The present Example provides for preliminary wet strength and dispersibility testing of CMC-bonded nonwoven materials including cellulose fibers. Binder formulations including various carboxymethyl cellulose (CMC) types in combination with calcium chloride ($CaCl_2$) as a metallic ion were prepared. The binder formulations were applied to cellulose handsheets prepared using a CPF (Cellulose Pad Former) to form a hydrogen-bonded web including 100% cellulose fibers (SSK grade, 4725 from Georgia Pacific). The binder formulations were applied to the nonwoven materials at various levels and in a variety of ways including: (i) CMC sprayed onto the web, dried, then calcium chloride sprayed onto the web, and dried a second time; (ii) CMC sprayed onto the web, followed by calcium chloride sprayed onto the web, then dried; and (iii) CMC mixed with calcium chloride, sprayed onto the web as a mixture, and dried. The resulting webs were tested for wet strength and dispersibility and were unsatisfactory in either wet strength, dispersibility, or both.

The binder was a 1000 mL solution of carboxymethylcellulose (CMC) (Blanose 7L1C1) with calcium chloride ($CaCl_2$). The binder had a CMC to calcium chloride ratio of approximately 3:1. The as-is pH of the binder was approximately 4.9 to 4.95. The formulation of the binder is provided in Tables 1A and 1B.

TABLE 1A

Binder Formulation

| Ingredient | Amount (g) |
|---|---|
| Carboxyl methylcellulose (CMC) | 75 g |
| Calcium Chloride ($CaCl_2$) | 25 g |
| Water | 925 g |

TABLE 1B

Binder Formulation

| Lb/gal | Total (gal) | Total Weight of 4.5 gallons | Solids (%) | Total Solids Weight (lb) | 3 parts 0.75 Blanose (lb) | 1 part 0.25 CaCl2 (lb) | Water (lb) | Total Solids (%) |
|---|---|---|---|---|---|---|---|---|
| 8.345 | 4.5 | 37.5525 | 0.05 | 1.878 | 1.408 | 0.469 | 35.67 | 5 |

To prepare the samples, one side of the sample material was sprayed with the binder solution, placed on a vacuum box for 3 seconds, and then dried in a thru-air oven for 3 minutes at 135° C. The second side of the sample material was then sprayed at the same sequence as provided above. The samples were prepared in accordance with Table 2.

TABLE 2

Samples 1-1 to 1-8 Preparation

| Sample | Oven Temperature (° C.) | Blanose 7L1C1 (pH) | Sample Area (sq. m) | Sample Weight (g) | Sample Basis Weight (gsm) | Sprayed CPF Weight (g) | Add-on Rate (%) | Basis Weight Sprayed CPF (gsm) | Solids Sprayed (g) |
|---|---|---|---|---|---|---|---|---|---|
| 1-1 | 135 | 4.37 | 0.092903 | 5.2814 | 56.8 | 5.8552 | 9.8 | 63.0 | 0.5738 |
| 1-2 | 135 | 3.19 | 0.092903 | 5.3091 | 57.1 | 6.1829 | 14.1 | 66.6 | 0.8738 |
| 1-3 | 135 | 3.79 | 0.092903 | 5.2880 | 56.9 | 6.1301 | 13.7 | 66.0 | 0.8421 |
| 1-4 | 135 | 4.37 | 0.092903 | 5.3118 | 57.2 | 6.1258 | 13.3 | 65.9 | 0.8140 |
| 1-5 | 135 | 4.91 | 0.092903 | 5.2891 | 56.9 | 6.2332 | 15.1 | 67.1 | 0.9441 |
| 1-6 | 135 | 5.55 | 0.092903 | 5.2426 | 56.4 | 6.0677 | 13.6 | 65.3 | 0.8251 |
| 1-7 | 135 | 6.42 | 0.092903 | 5.3018 | 57.1 | 6.1629 | 14.0 | 66.3 | 0.8611 |
| 1-8 | 135 | 7.62 | 0.092903 | 5.2608 | 56.6 | 6.0695 | 13.3 | 65.3 | 0.8087 |

Cationic and Anionic Lotion Addition

The samples were tested for strength with the addition of a cationic lotion or an anionic lotion using Thwing-Albert EJA Series Tester. Each of the samples was about 1 inch wide and about 4 inches long. The lotions were added at three (3) times the weight of the sample. The cationic lotion had a pH of 7.76 and the anionic lotion had a pH of 8.18. The lotioned tensile strength was tested at varying pH levels of the binder solution as provided in Tables 1A and 1B, including CMC and calcium chloride. The strength test parameters are provided in Table 3.

TABLE 3

Strength Test Parameters

| CPF Hand-sheet | Blanose 7L1C1 (pH) | Basis Weight CPF Handsheet (gsm) | Add-on Rate (%) | Basis Weight Sprayed CPF (gsm) | Solids Sprayed (grams) | 24% pH | Ethanol % in Lotion 26% pH | 29% pH |
|---|---|---|---|---|---|---|---|---|
| 1-2 | 3.19 | 57.1 | 14.1 | 66.6 | 0.8738 | 57 | 116 | 221 |
| 1-3 | 3.79 | 56.9 | 13.7 | 66.0 | 0.8421 | 79 | 205 | 308 |
| 1-4 | 4.37 | 57.2 | 13.3 | 65.9 | 0.8140 | 149 | 291 | 412 |
| 1-5 | 4.91 | 56.9 | 15.1 | 67.1 | 0.9441 | 112 | 104 | 180 |
| 1-6 | 5.55 | 56.4 | 13.6 | 65.3 | 0.8251 | 71 | 129 | 229 |
| 1-7 | 6.42 | 57.1 | 14.0 | 66.3 | 0.8611 | 57 | 145 | 201 |
| 1-8 | 7.62 | 56.6 | 13.3 | 65.3 | 0.8087 | 53 | 160 | 200 |

Figure 1:
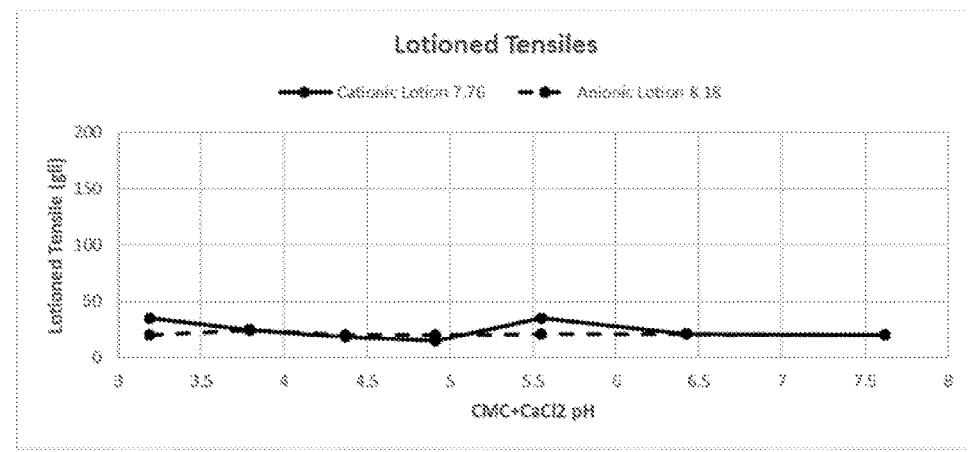
FIG. 1 depicts the wet strength testing results of cellulose-based nonwoven materials including cationic and anionic lotions and binders at varying levels of pH prepared in accordance with certain non-limiting embodiments as provided in Example 1.

The results are provided in FIG. 1 and Table 4.

TABLE 4

Strength Test Results

| Sample | CMC (Blanose 7L1C1) with $CaCl_2$ 3:1 | Add-on Rate (%) | Basis Weight Sprayed CPF (gsm) | Cationic (gli) | Anionic (gli) |
|---|---|---|---|---|---|
| 1-2 | 3.19 | 14.1 | 66.6 | 35 | 20 |
| 1-3 | 3.79 | 13.7 | 66.0 | 25 | 25 |
| 1-4 | 4.37 | 13.3 | 65.9 | 19 | 20 |
| 1-5 | 4.91 | 15.1 | 67.1 | 15 | 20 |
| 1-6 | 5.55 | 13.6 | 65.3 | 35 | 21 |
| 1-7 | 6.42 | 14.0 | 66.3 | 21 | 21 |
| 1-8 | 7.62 | 13.3 | 65.3 | 20 | 20 |

As provided in Table 4 and FIG. 1, the cationic and anionic lotions did not have an effect on wet strength of the nonwoven material with varied pH of the CMC and calcium chloride binder solution.

Cationic Lotion with Alcohol Addition

The samples were tested for strength with the addition of a cationic lotion including varying levels of alcohol (10% Ethanol, 20% Ethanol, 24% Ethanol, 26% Ethanol, and 29% Ethanol). The cationic lotion was added at three (3) times the weight of the sample. The cationic lotion had a pH of 7.76 with no adjustments. The 10% Ethanol and cationic lotion solution had a pH of 7.91. With the addition of Ethanol at 24-29%, the pH of the lotion ranged from 8-8.12. The 20% Ethanol solution had a pH of 7.96. The 24% Ethanol solution had a pH of 8. The 26% Ethanol solution had a pH of 8.12. The 29% Ethanol solution had a pH of 8.06. The lotioned tensile strength was tested at varying pH levels of the binder solution as provided in Tables 1A and 1B, including CMC and calcium chloride. The binder had a CMC to calcium chloride ratio of approximately 3:1. The pH of Sample 1-5 was about 4.95.

Figure 2A:
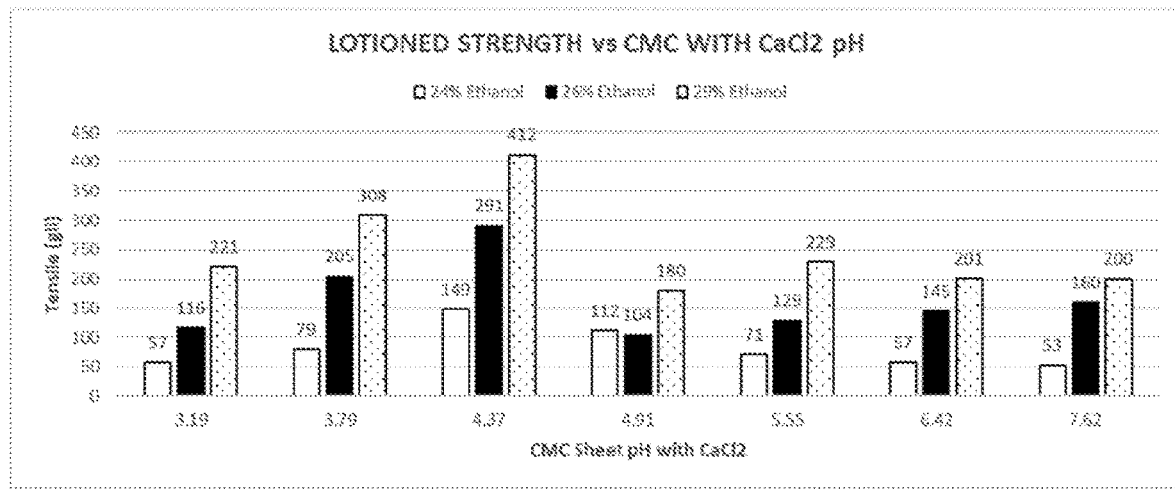
FIG. 2A depicts the wet strength testing results of cellulose-based nonwoven materials including binders at varying levels of pH including alcohol prepared in accordance with certain non-limiting embodiments as provided in Example 1.
Figure 2B:
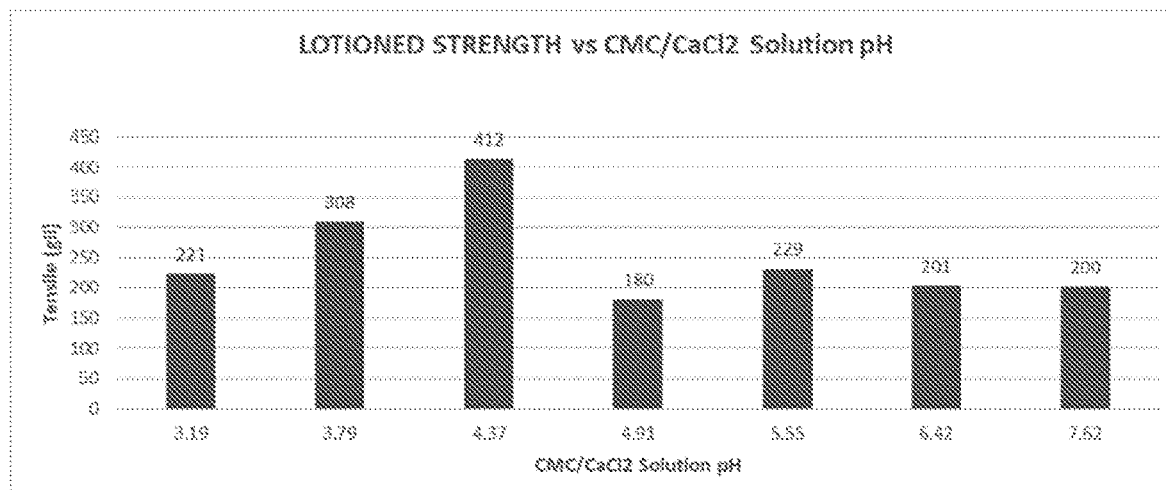
FIG. 2B depicts the wet strength testing results of nonwoven materials including binders at varying levels of pH prepared in accordance with certain non-limiting embodiments as provided in Example 1.

The results are provided in Table 5 and FIGS. 2A and 2B. FIG. 2A provides the results for the addition of cationic lotion and 24% Ethanol, 26% Ethanol, or 29% Ethanol. FIG. 2B provides the results for the addition of cationic lotion and 29% Ethanol addition.

TABLE 5

| | Lotioned Strength Results (Lotion and Alcohol Addition) | | | | |
|---|---|---|---|---|---|
| Sample | 10% Ethanol (7.91 pH) (gli) | 20% Ethanol (7.96 pH) (gli) | 24% Ethanol (8.00 pH) (gli) | 26% Ethanol (8.12 pH) (gli) | 29% Ethanol (8.06 pH) (gli) |
| 1-1 | 22 | — | 79 | 163 | 223 |
| 1-2 | — | — | 57 | 116 | 221 |
| 1-3 | — | — | 79 | 205 | 308 |
| 1-4 | 21 | — | 149 | 291 | 412 |
| 1-5 | 23 | 59 | 112 | 104 | 180 |
| 1-6 | — | — | 71 | 129 | 229 |
| 1-7 | — | — | 57 | 145 | 201 |
| 1-8 | — | — | 53 | 160 | 200 |

Binders including CMC and calcium chloride in a specific pH range with the addition of lotion and alcohol provided for increased strength in nonwoven materials. Further, as provided in Table 4, Sample 1-5 (4.91 pH) had reduced strength at 26% and 29% Ethanol solutions as compared to Samples 1-4 (4.4 pH) and Sample 1-3 (3.8 pH). At 26% and 29% Ethanol, Sample 1-3 had a tensile strength of 205 gli and 308 gli, respectively, and Sample 1-9 had a tensile strength of 291 gli and 412 gli, respectively. Sample 1-5, with a pH of 4.91, had a significantly lower tensile strength at 26% and 29% Ethanol, at 104 gli and 180 gli, respectively. The appropriate range for the CMC and calcium chloride binder solution is 4.3 to 4.5 pH. As provided in FIGS. 2A and 2B, strength of the nonwoven material is affected with alcohol content. For CMC-based binders, the binder with at least 26% alcohol provided increased performance with respect to tensile strength with reducing a water content in the lotion increased lotioned tensile strength. A further sample was tested with 80% Ethanol on a nonwoven material including cellulose fibers, which resulted in a lotioned strength of about 800 gli.

Through further experimentation, satisfactory wet strength and dispersibility was simultaneously achieved if the pH of the binder including CMC and calcium chloride was between 4.3 and 4.5.

Lotion pH and CMC/CaCl$_2$ Binder Solution pH

The samples were tested for strength with varying cationic lotion pH levels. The lotioned tensile strength was tested at varying pH levels of the binder solution as provided in Tables 1A and 1B, including CMC and calcium chloride. The lotion was added at three (3) times the weight of the samples.

Figure 3:
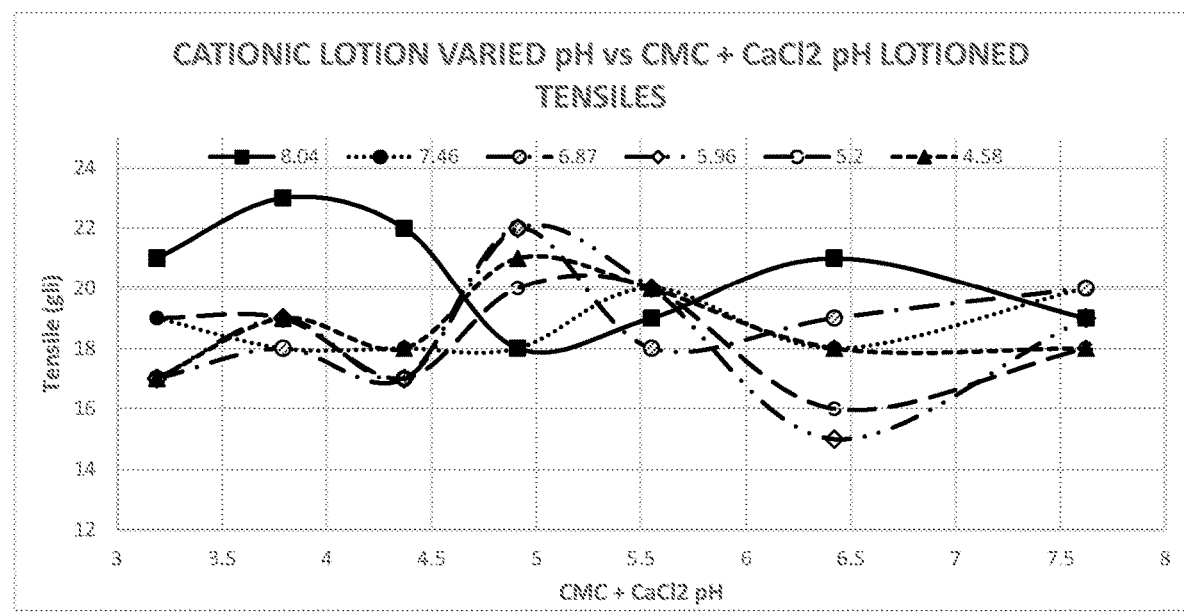
FIG. 3 depicts the wet strength testing results of nonwoven materials including binders at varying levels of pH prepared in accordance with certain non-limiting embodiments as provided in Example 1.

The results are provided in Table 6 and FIG. 3. FIG. 3 excludes the results for Sample 1-1

As provided in Table 6 and FIG. 3, the cationic lotion with varied pH has no effect on the wet strength with the varied pH of the binder solution including CMC and calcium chloride.

Example 2: CMC-Bonded Nonwoven Materials (Cellulose)—Wet Strength and Dispersibility The present Example provides for wet strength and dispersibility testing of cellulose-based and modified cellulose-based nonwoven materials bonded with binders either including carboxymethylcellulose (CMC) or including CMC and calcium chloride (CaCl$_2$). The lotion was added in an amount of three (3) times the weight of the sample. All binder solutions had a pH of about 4.4. Samples A-1 to A-10 included cellulose fibers (SSK grade, 4725 from Georgia Pacific). Samples B-1 to B-10 included modified cellulose fibers (FFLE). Samples A1-A5 and B1-B5 were bonded with a binder including carboxymethylcellulose (CMC). Samples A6-A10 and B6-B10 were bonded with a binder including CMC and calcium chloride.

The samples including cellulose fibers were prepared in accordance with Table 7.

TABLE 6

| | Lotioned Strength Test Results | | | | | | | |
|---|---|---|---|---|---|---|---|---|
| Sample | CMC (Blanose 7L1C1) with CaCl$_2$ 3:1 (pH) | Add-On Rate (%) | Basis Weight Sprayed CPF (gsm) | Lotion 8.04 pH (gli) | Lotion 7.46 pH (gli) | Lotion 6.87 pH (gli) | Lotion 5.96 pH (gli) | Lotion 5.2 pH (gli) | Lotion 4.58 pH (gli) |
| 1-1 | 4.37 | 9.8 | 63.0 | 22 | 22 | 19 | 19 | 19 | 16 |
| 1-2 | 3.19 | 14.1 | 66.6 | 21 | 19 | 17 | 17 | 19 | 17 |
| 1-3 | 3.79 | 13.7 | 66.0 | 23 | 18 | 18 | 19 | 19 | 19 |
| 1-4 | 4.37 | 13.3 | 65.9 | 22 | 18 | 17 | 17 | 17 | 18 |
| 1-5 | 4.91 | 15.1 | 67.1 | 18 | 18 | 22 | 22 | 20 | 21 |
| 1-6 | 5.55 | 13.6 | 65.3 | 19 | 20 | 18 | 20 | 20 | 20 |
| 1-7 | 6.42 | 14.0 | 66.3 | 21 | 18 | 19 | 15 | 16 | 18 |
| 1-8 | 7.62 | 13.3 | 65.3 | 19 | 20 | 20 | 19 | 18 | 18 |

TABLE 7

Sample Preparation (Cellulose Fibers)

| Sample | Oven Temp. (° C.) | CMC Blanose 7L1C1 (pH) | Sample Area (sq. m) | Sample Weight (g) | Sample Basis Weight (gsm) | Sprayed CPF Weight (g) | Add-on Rate (%) | Basis Weight Sprayed CPF (gsm) | Solids Sprayed (g) |
|---|---|---|---|---|---|---|---|---|---|
| A-1 | 135 | 4.39 | 0.092903 | 5.2139 | 56.1 | 5.9844 | 12.9 | 64.4 | 0.7705 |
| A-2 | 135 | 4.39 | 0.092903 | 5.1266 | 55.2 | 5.7457 | 10.8 | 61.8 | 0.6191 |
| A-3 | 135 | 4.39 | 0.092903 | 5.1252 | 55.2 | 5.9189 | 13.4 | 63.7 | 0.7937 |
| A-4 | 135 | 4.39 | 0.092903 | 5.1288 | 55.2 | 5.9301 | 13.5 | 63.8 | 0.8013 |
| A-5 | 135 | 4.39 | 0.092903 | 5.1224 | 55.1 | 5.8963 | 13.1 | 63.5 | 0.7739 |
| A-6 | 135 | 4.40 | 0.092903 | 5.1252 | 55.2 | 5.9028 | 13.2 | 63.5 | 0.7776 |
| A-7 | 135 | 4.40 | 0.092903 | 5.1744 | 55.7 | 6.0865 | 15.0 | 65.5 | 0.9121 |
| A-8 | 135 | 4.40 | 0.092903 | 5.1229 | 55.1 | 5.9548 | 14.0 | 64.1 | 0.8319 |
| A-9 | 135 | 4.40 | 0.092903 | 5.1293 | 55.2 | 5.8630 | 12.5 | 63.1 | 0.7337 |
| A-10 | 135 | 4.40 | 0.092903 | 5.1034 | 54.9 | 5.9266 | 13.9 | 63.8 | 0.8232 |

The samples including modified cellulose fibers were prepared in accordance with Table 8.

TABLE 8

Sample Preparation (Modified Cellulose Fibers)

| Sample | Oven Temp. (° C.) | CMC Blanose 7L1C1 (pH) | Sample Area (sq. m) | Sample Weight (g) | Sample Basis Weight (gsm) | Sprayed CPF Weight (g) | Add-on Rate (%) | Basis Weight Sprayed CPF (gsm) | Solids Sprayed (g) |
|---|---|---|---|---|---|---|---|---|---|
| B-1 | 135 | 4.39 | 0.092903 | 4.9612 | 53.4 | 5.6958 | 12.9 | 61.3 | 0.7346 |
| B-2 | 135 | 4.39 | 0.092903 | 5.0138 | 54.0 | 5.7809 | 13.3 | 62.2 | 0.7671 |
| B-3 | 135 | 4.39 | 0.092903 | 5.0334 | 54.2 | 5.7842 | 13.0 | 62.3 | 0.7508 |
| B-4 | 135 | 4.39 | 0.092903 | 4.9886 | 53.7 | 5.7560 | 13.3 | 62.0 | 0.7674 |
| B-5 | 135 | 4.39 | 0.092903 | 5.0703 | 54.6 | 5.8754 | 13.7 | 63.2 | 0.8051 |
| B-6 | 135 | 4.40 | 0.092903 | 5.0328 | 54.2 | 5.6266 | 10.6 | 60.6 | 0.5938 |
| B-7 | 135 | 4.40 | 0.092903 | 5.0198 | 54.0 | 5.8291 | 13.9 | 62.7 | 0.8093 |
| B-8 | 135 | 4.40 | 0.092903 | 5.0226 | 54.1 | 5.8245 | 13.8 | 62.7 | 0.8019 |
| B-9 | 135 | 4.40 | 0.092903 | 5.0122 | 54.0 | 5.8414 | 14.2 | 62.9 | 0.8292 |
| B-10 | 135 | 4.40 | 0.092903 | 4.9920 | 53.7 | 5.8268 | 14.3 | 62.7 | 0.8348 |

Strength Testing

The samples were tested for dry tensile strength and elongation and lotioned tensile strength and elongation using Thwing-Albert EJA Series Tester. Each of the samples was about 1 inch wide and about 4 inches long. Samples A-6 to A-10 were additionally tested with an anionic lotion for tensile strength and elongation.

The strength test results for the cellulose-based materials are provided in Table 9.

TABLE 9

Strength Test Results (Cellulose Fibers)

| Sample | Dry Tensile (gli) | Dry Elongation (%) | Cationic with Ethanol Tensile (gli) | Cationic with Ethanol Elongation (%) | Anionic with Ethanol Tensile (gli) | Anionic with Ethanol Elongation (%) |
|---|---|---|---|---|---|---|
| A-1 | 911 | 4 | 19 | 7 | — | — |
| A-2 | 1379 | 4 | 17 | 15 | — | — |
| A-3 | 1992 | 4 | 15 | 11 | — | — |
| A-4 | 2154 | 3 | 14 | 8 | — | — |
| A-5 | 1336 | 3 | 16 | 10 | — | — |
| Average (A1-A5) | 1554 | 4 | 16 | 10 | — | — |
| A-6 | 1009 | 2 | 224 | 11 | 94 | 6 |
| A-7 | 1878 | 3 | 423 | 13 | 127 | 6 |
| A-8 | 1614 | 3 | 364 | 15 | 140 | 8 |
| A-9 | 1704 | 3 | 307 | 14 | 89 | 5 |
| A-10 | 1767 | 3 | 343 | 9 | 132 | 6 |
| Average (A6-A10) | 1594 | 3 | 332 | 12 | 116 | 6 |

The strength test results for the modified cellulose-based materials are provided in Table 10.

TABLE 10

Strength Test Results (Modified Cellulose Fibers)

| Sample | Dry Tensile (gli) | Dry Elongation (%) | Cationic with Ethanol Tensile (gli) | Cationic with Ethanol Elongation (%) |
|---|---|---|---|---|
| B-1 | 1500 | 3 | 13 | 5 |
| B-2 | 1385 | 3 | 17 | 8 |

TABLE 10-continued

Strength Test Results (Modified Cellulose Fibers)

| Sample | Dry Tensile (gli) | Dry Elongation (%) | Cationic with Ethanol Tensile (gli) | Cationic with Ethanol Elongation (%) |
|---|---|---|---|---|
| B-3 | 1591 | 3 | 14 | 11 |
| B-4 | 1781 | 3 | 19 | 11 |
| B-5 | 1144 | 3 | 12 | 7 |
| Average (B1-B5) | 1480 | 3 | 15 | 8 |
| B-6 | 625 | 3 | 81 | 7 |
| B-7 | 771 | 2 | 96 | 7 |
| B-8 | 654 | 3 | 78 | 5 |
| B-9 | 1058 | 2 | 115 | 6 |
| B-10 | 812 | 3 | 89 | 7 |
| Average (B6-B10) | 784 | 3 | 92 | 6 |

Figure 4:
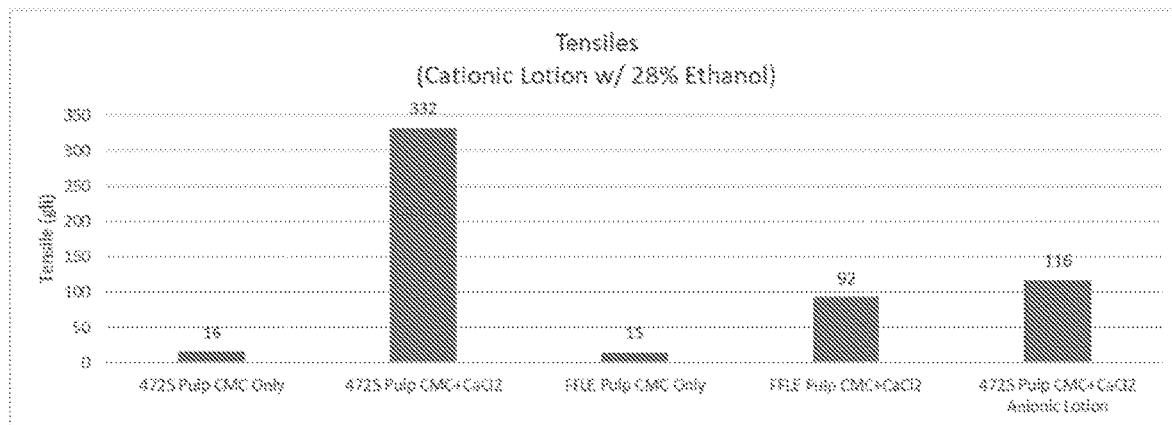
FIG. 4 depicts the wet strength testing results of various nonwoven materials including binders prepared in accordance with certain non-limiting embodiments as provided in Example 2.

The strength results for all samples are provided in FIG. 4. The CMC-based binder without calcium chloride and lotion did not provide adequate strength. Testing using anionic lotion provided a reduction in strength than the cationic lotion (both with Ethanol). The CMC-based binder with calcium chloride in a cationic lotion with Ethanol provided for adequate strength.

Dispersibility Testing

Samples A-6 to A-10 including a cellulose nonwoven material with a CMC and calcium chloride binder (pH 4.40) in a cationic lotion with Ethanol were further tested for dispersibility. All samples completely dispersed within a few seconds of being shaken in a container including 700 mL of tap water.

Example 3: CMC-Bonded Nonwoven Materials with Varying Binder pH—Strength and Dispersibility The present Example provides for dispersibility and strength (wet and dry) testing of nonwoven materials with binder formulations at varying pH. The binder included carboxymethylcellulose (CMC), calcium chloride ($CaCl_2$)) and water in their proportions and amounts as provided in Table 11. The ratio of CMC:$CaCl_2$) in the binder was approximately 1:1.

TABLE 11

Binder Formulation

| Additive | Grams | % of Total | % Solids |
|---|---|---|---|
| CMC | 13.42 | 2.68 | 5.00 |
| $CaCl_2$ | 11.56 | 2.31 | |
| Water | 475.01 | 95.00 | |
| Total | 500.00 | 100.00 | |

Samples 3-1 to 3-8 were prepared. The samples were cationized pulp fibers (CPF) handsheets including cellulose fibers (Leaf River 4725, Georgia Pacific). One side of the handsheet was sprayed with the binder solution, placed on a vacuum box for 3 seconds, and then dried in a thru-air oven for 3 minutes at 120° C. The second side of the handsheet was then sprayed at the same sequence as above followed. The spray add-on rate was 13%. The binder recipe was made to deliver 7% CMC and 6% $CaCl_2$ to the handsheet. Samples 3-1 to 3-4 included binder with carboxymethyl cellulose (CMC), calcium chloride ($CaCl_2$), and water with no pH adjustment (6.65 pH). Samples 3-5 to 3-8 included binder with carboxymethyl cellulose (CMC), calcium chloride ($CaCl_2$), and water with no pH adjustment (4.35 pH). The sample preparation of Samples 3-1 to 3-8 is provided in Table 12.

TABLE 12

Samples 3-1 to 3-8 Preparation

| Sample | Weight (g) | Basis Weight (gsm) | Target Dry Addition Per Side (g) | Target Wet Addition Per Side (g) | Wet Spray Weight Side 1 (g) | Wet Spray Weight Side 2 (g) | Total Sheet Weight (g) | Total Dry Basis Weight with Additives (g) | Total Dry Add-On (%) |
|---|---|---|---|---|---|---|---|---|---|
| 3-1 | 5.0175 | 54.0 | 0.32614 | 5.32 | 5.47 | 5.87 | 5.8516 | 63.0 | 14.3 |
| 3-2 | 5.0417 | 54.3 | 0.32771 | 5.35 | 5.51 | 5.91 | 5.9272 | 63.8 | 14.9 |
| 3-3 | 5.0195 | 54.0 | 0.32627 | 5.32 | 5.60 | 5.67 | 5.8474 | 62.9 | 14.2 |
| 3-4 | 5.0190 | 54.0 | 0.32624 | 5.32 | 5.51 | 5.79 | 5.8601 | 63.1 | 14.4 |
| 3-5 | 5.0253 | 54.1 | 0.32664 | 5.33 | 5.61 | 5.68 | 5.8485 | 63.0 | 14.1 |
| 3-6 | 5.0129 | 54.0 | 0.32584 | 5.32 | 6.53 | 4.52 | 5.8186 | 62.6 | 13.8 |
| 3-7 | 5.0766 | 54.6 | 0.32998 | 5.38 | 5.43 | 5.67 | 5.8768 | 63.3 | 13.6 |
| 3-8 | 5.0279 | 54.1 | 0.32681 | 5.33 | 5.46 | 5.65 | 5.8512 | 63.0 | 14.1 |

Dispersibility Testing

The samples were placed in a slosh box (3 box set up) as described in the IWSFG PAS 3B:2017-Disintegration Test Methods-Slosh Box, which is incorporated by reference herein in its entirety. Water in an amount of 8 L was added to each box. The time to disperse (s) was measured. Five specimens of each sample were tested.

Strength Testing

The samples were tested for tensile strength and elongation both in a dry and lotioned conditions using Thwing-Albert EJA Series Tester. Each of the samples was about 1 inch wide and about 4 inches long.

The dispersibility test results are provided in Table 13.

TABLE 13

Dispersibility Test Results (4.35 pH and 6.65 pH Binders)

| Sample | Binder pH | 8" × 7" Weight (g) | Basis Weight (gsm) | Time to Disperse (s) | % Through 6.3 mm Sieve (%) |
|---|---|---|---|---|---|
| 3-2 | 6.65 | 2.3255 | 64.4 | ≤22 | 100 |
| 3-3 | 6.65 | 2.3387 | 64.7 | ≤18 | 100 |
| 3-4 | 6.65 | 2.1437 | 59.3 | ≤19 | 100 |
| 3-6 | 4.35 | 2.3053 | 63.8 | ≤18 | 100 |
| 3-7 | 4.35 | 2.3784 | 65.8 | ≤18 | 100 |
| 3-8 | 4.35 | 2.4171 | 66.9 | ≤18 | 100 |

The strength test results of individual tensile strips for the 6.65 pH binder samples of the present Example are provided in Table 14.

TABLE 14

Strength Test Results (6.65 pH Binder)

| | Dry | | | | 40% Ethanol | | |
|---|---|---|---|---|---|---|---|
| 1" × 4" Strip Weight (g) | Basis Weight (gsm) | Dry Tensile (gli) | Dry Elongation (%) | 1" × 4" Strip Weight (g) | Basis Weight (gsm) | Ethanol Tensile (gli) | Ethanol Elongation (%) |
| 0.1758 | 68.1 | 1587 | 12 | 0.1646 | 63.8 | 284 | 12 |
| 0.1714 | 66.4 | 1750 | 14 | 0.1809 | 70.1 | 350 | 14 |
| 0.1734 | 67.2 | 1426 | 12 | 0.1678 | 65.0 | 325 | 13 |
| 0.1726 | 66.9 | 1640 | 13 | 0.1784 | 69.1 | 312 | 14 |
| 0.1723 | 66.8 | 1441 | 11 | 0.1727 | 66.9 | 273 | 12 |
| 0.1686 | 65.3 | 1452 | 13 | 0.1662 | 64.4 | 308 | 13 |
| 0.1707 | 66.1 | 1514 | 12 | 0.1761 | 68.2 | 324 | 12 |
| 0.1673 | 64.8 | 1287 | 11 | 0.1769 | 68.5 | 272 | 12 |
| 0.1695 | 65.7 | 1505 | 14 | 0.175 | 67.8 | 387 | 15 |
| 0.1733 | 67.2 | 1148 | 12 | 0.1802 | 69.8 | 357 | 11 |
| Average | 66.5 | 1475 | 12 | | 67.4 | 319 | 13 |

The strength test results of individual tensile strips for the 4.35 pH binder samples of the resent Example are provided in Table 15.

TABLE 15

Test Results 4.35pH Binder

| | Dry | | | | 40% Ethanol | | |
|---|---|---|---|---|---|---|---|
| 1" × 4" Strip Weight (g) | Basis Weight (gsm) | Dry Tensile (gli) | Dry Elongation (%) | 1" × 4" Strip Weight (g) | Basis Weight (gsm) | Ethanol Tensile (gli) | Ethanol Elongation (%) |
| 0.1781 | 69.0 | 1612 | 12 | 0.1715 | 66.5 | 322 | 13 |
| 0.1686 | 65.3 | 1332 | 13 | 0.1751 | 67.9 | 409 | 15 |
| 0.1747 | 67.7 | 1519 | 12 | 0.1697 | 65.8 | 366 | 12 |
| 0.1800 | 69.8 | 1709 | 12 | 0.173 | 67.0 | 416 | 13 |
| 0.1698 | 65.8 | 1256 | 11 | 0.1732 | 67.1 | 392 | 12 |
| 0.1691 | 65.5 | 1290 | 10 | 0.1699 | 65.8 | 322 | 11 |
| 0.1775 | 68.8 | 1489 | 11 | 0.1701 | 65.9 | 382 | 12 |
| 0.1792 | 69.4 | 1518 | 12 | 0.1733 | 67.2 | 427 | 12 |
| 0.1671 | 64.8 | 1242 | 11 | 0.1656 | 64.2 | 299 | 13 |
| 0.1792 | 69.4 | 1604 | 12 | 0.1794 | 69.5 | 418 | 11 |
| Average | 67.6 | 1457 | 12 | | 66.7 | 375 | 12 |

The average lotioned tensile strength for samples was higher in the 4.35 pH binder (375 gli) than the 6.65 pH binder (319 gli). Dispersibility results provided that samples with both binders quickly dispersed in a slosh box test.

Example 4: CMC-Bonded Nonwoven Materials (Modified Cellulose)—Wet Strength and Dispersibility The present Example provides for wet strength and dispersibility testing of CMC-bonded nonwoven materials including modified cellulose fibers. The modified cellulose fibers included cellulose fibers precipitated with Aluminum as a metallic ion. Each of the samples included 3 layers of modified cellulose fibers. Each of the samples included a same type of modified cellulose fibers. The binder was applied to the surface of the outer layers. Two different modified cellulose fiber types were tested: FFLE from Georgia Pacific Cellulose (Sample 4-1) and Valance from International Paper (Sample 4-2). Each of the samples included a binder including 9.75% CMC and 3.25% $CaCl_2$) based on the total weight of the sheet adjusted to pH of 4.33 and applied as a solution containing 5% solids. Each sample was tested in comparison to a control including unmodified cellulose fibers from Georgia Pacific Leaf River 4725.

Wet Strength Testing

Figure 5A:
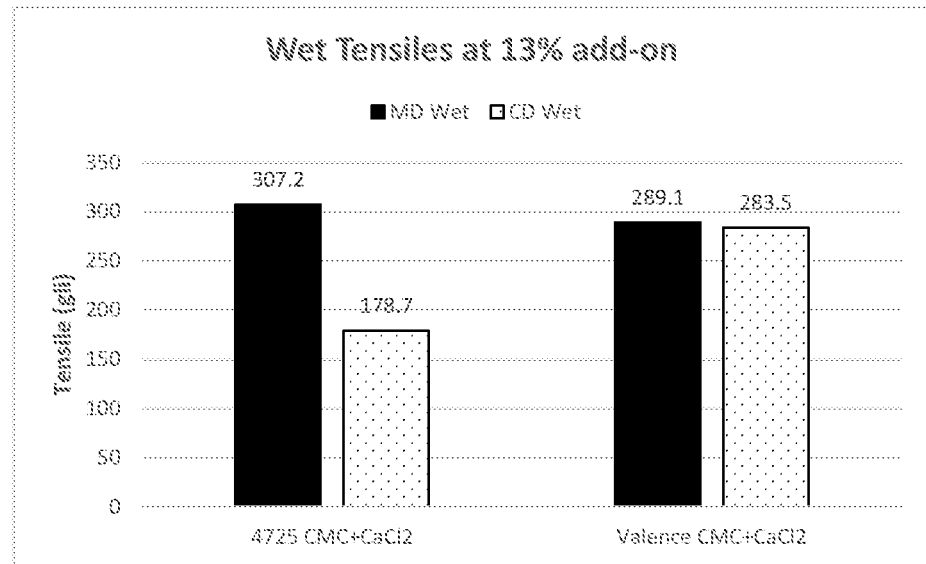
FIG. 5A depicts the wet strength testing results of modified cellulose-based nonwoven materials including binders prepared in accordance with certain non-limiting embodiments as provided in Example 4.
Figure 5B:
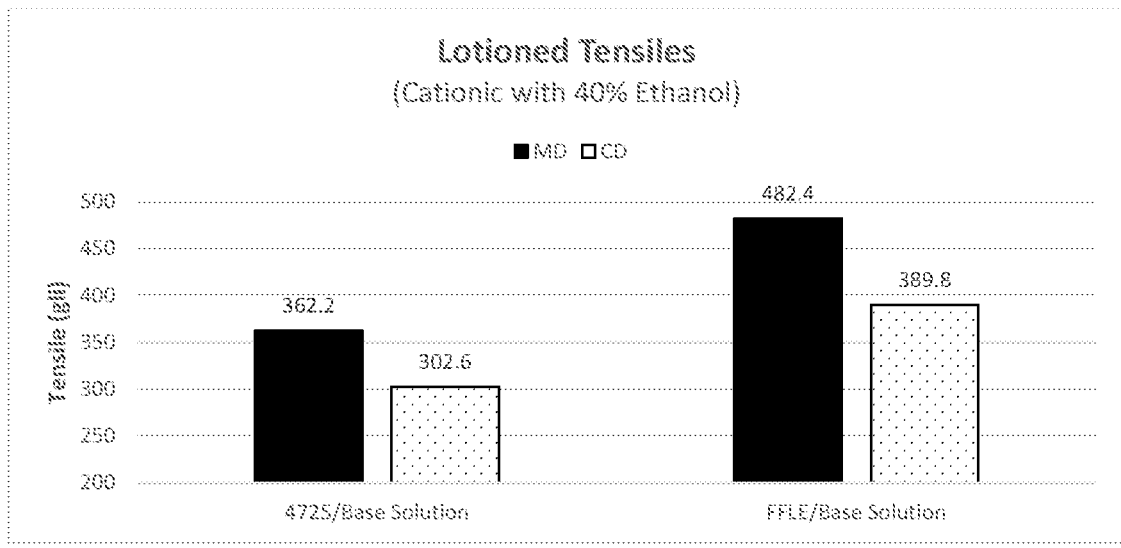
FIG. 5B depicts the wet strength testing results of modified cellulose-based nonwoven materials including binders prepared in accordance with certain non-limiting embodiments as provided in Example 4.

Each sample was tested for wet strength as provided in Example 1. The results for wet strength testing are provided in FIGS. 5A and 5B. As shown in FIG. 5A, Sample 4-2 (Valence) had a 37% increase in cross-directional (CD) tensile strength as compared to the control. As shown in FIG. 5B, Sample 4-1 (FFLE) had a 25% increase in machine directional (MD) tensile strength as compared to the control. Sample 4-1 (FFLE) also had a 22% increase in cross-directional (CD) tensile strength as compared to the control.

The wet strength and dispersibility of CMC-bonded nonwoven materials depended at least in part on the presence of a suitable metallic ion. The properties of the CMC-bonded nonwoven of wet strength and dispersibility were improved by using modified cellulose fibers which were precipitated with a suitable metallic ion.

Example 5: CMC-Bonded Nonwoven Materials with Surfactants and Other Additives (Plasticizers)—Strength The present Example provides for the addition of various surfactants and other additives such as plasticizers to the CMC-based binder solution prior to application onto the nonwoven material. The nonwoven material included 100% cellulose fibers (SSK grade, 4725 from Georgia Pacific). The control included the nonwoven material bonded with a base solution including 9.75% carboxymethylcellulose (CMC) and 3.25% calcium chloride based on total substrate weight in a 5% solution which was applied to the nonwoven material and dried. Sample 6-1 was a nonwoven material with 100% cellulose fibers (SSK grade, 4725 from Georgia Pacific). Sample 6-1 was bonded with the base solution which further included a surfactant (Aerosol OT-75, Cytec Industries, Inc.). The resulting mixture was applied to an unbonded nonwoven material, and dried. Sample 6-2 was a nonwoven material with 100% cellulose fibers (SSK grade, 4725 from Georgia Pacific). Sample 6-2 was bonded with the base solution including 9.75% carboxymethylcellulose (CMC) and 3.25% calcium chloride based on a total substrate weight in a 5% solution which further included a surfactant (Aerosol OT-75, Cytec Industries, Inc., 1.8% based on a total substrate weight in a 5% solution) and a plasticizer, polyethylene glycol (PEG) (PEG-200, CARBOWAX, Dow Chemical Co, 3.0% of the total substrate weight with the solution containing 5% solids. Cellulose fibers were airlaid and the binder solutions were sprayed on both outer layers of the substrate.

The nonwoven materials was tested for wet strength and elongation as provided herein. The results of the strength and elongation testing are provided in FIGS. 6A and 6B.

The addition of a surfactant to the base solution resulted in a CMC-bonded nonwoven material with comparative performance. The addition of the surfactant also improved the softness of the nonwoven material as judged by a panel of users as compared to the control nonwoven material including the untreated base solution. As shown in FIG. 6B, the plasticizer improved the elongation of the nonwoven material. It was also observed that the addition of the plasticizer improved the ability to wind the nonwoven material onto a roll.

In addition to the various embodiments depicted and claimed, the disclosed subject matter is also directed to other embodiments having other combinations of the features disclosed and claimed herein. As such, the particular features presented herein can be combined with each other in other manners within the scope of the disclosed subject matter such that the disclosed subject matter includes any suitable combination of the features disclosed herein. The foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the systems and methods of the disclosed subject matter without departing from the spirit or scope of the disclosed subject matter. Thus, it is intended that the disclosed subject matter include modifications and variations that are within the scope of the appended claims and their equivalents.

Various patents and patent applications are cited herein, the contents of which are hereby incorporated by reference herein in their entireties.

What is claimed is:

1. A nonwoven material comprising:
   at least one layer comprising cellulose fibers, synthetic fibers, or any combination thereof;
   a binder covering at least a portion of the at least one layer, wherein the binder comprises carboxymethyl cellulose and a metallic salt, and the binder has a pH ranging from about 4.3 to about 4.5; and
   a lotion, the lotion comprising from 24 to 29 wt % of ethanol.

2. The nonwoven material of claim 1, wherein the binder has a pH ranging from about 4.3 to about 4.4.

3. The nonwoven material of claim 1, wherein the binder has a pH ranging from about 4.4 to about 4.5.

4. The nonwoven material of claim 1, wherein the carboxymethyl cellulose and metallic salt are present in the binder in a weight:weight ratio of about 1:1.

5. The nonwoven material of claim 1, wherein the carboxymethyl cellulose and metallic salt are present in the binder in a weight:weight ratio of about 3:1.

6. The nonwoven material of claim 1, wherein the metallic salt comprises calcium chloride.

7. The nonwoven material of claim 1, wherein the binder further comprises a surfactant.

8. The nonwoven material of claim 1, wherein the binder further comprises a plasticizer.

9. The nonwoven material of claim 8, wherein the plasticizer comprises a polyethylene glycol.

10. The nonwoven material of claim 1, wherein the cellulose fibers comprise modified cellulose fibers, cellulose fluff, or eucalyptus pulp, or any combination thereof.

11. The nonwoven material of claim 1, wherein the cellulose fibers comprise softwood fibers, hardwood fibers, or a combination of softwoods fibers and hardwood fibers.

12. The nonwoven material of claim 1, wherein the synthetic fibers comprise bicomponent fibers.

13. The nonwoven material of claim 1, wherein the nonwoven material has a wet strength of from about 350 gli to about 400 gli.

14. A personal care product, comprising the nonwoven material of claim 1.

15. The personal care product of claim 14, wherein the personal care product is a wipe.

16. The nonwoven material of claim 1, wherein the lotion has a pH ranging from about 7 to about 9.

17. A nonwoven material comprising:
at least one layer comprising cellulose fibers, synthetic fibers, or any combination thereof;
a binder covering at least a portion of the at least one layer, wherein the binder has a pH ranging from about 4.3 to about 4.5 and comprises:
carboxymethyl cellulose; and
one or more metallic salts, the one or more metallic salts present in the binder in an amount ranging from about 15 to about 50 wt %, relative to the weight of the carboxymethyl cellulose; and
a lotion, the lotion comprising from 24 to 29 wt % of ethanol.

18. The nonwoven material of claim 17, wherein the one or more metallic salts are present in the binder in an amount ranging from about 25 to about 50 wt %, relative to the weight of the carboxymethyl cellulose.

* * * * *